United States Patent
Liu et al.

(10) Patent No.: US 10,456,581 B2
(45) Date of Patent: Oct. 29, 2019

(54) SINGLE PASS CORONARY VENOUS LEAD FOR MULTIPLE CHAMBER SENSE AND PACE

(71) Applicant: Cardiac Pacemakers, Inc., St. Paul, MN (US)

(72) Inventors: Lili Liu, Maple Grove, MN (US); Matthew J. Miller, Stillwater, MN (US); Kyle K. Hoecke, Lino Lakes, MN (US); Ronald W. Kunkel, Jim Falls, WI (US)

(73) Assignee: Cardiac Pacemakers, Inc, St Paul, MN (US)

( * ) Notice: Subject to any disclaimer, the term of this patent is extended or adjusted under 35 U.S.C. 154(b) by 187 days.

(21) Appl. No.: 15/356,137

(22) Filed: Nov. 18, 2016

(65) Prior Publication Data
US 2017/0143968 A1    May 25, 2017

Related U.S. Application Data

(60) Provisional application No. 62/258,392, filed on Nov. 20, 2015.

(51) Int. Cl.
*A61N 1/36* (2006.01)
*A61N 1/368* (2006.01)
(Continued)

(52) U.S. Cl.
CPC ........... *A61N 1/3684* (2013.01); *A61N 1/056* (2013.01); *A61N 1/0587* (2013.01); *A61N 1/362* (2013.01);
(Continued)

(58) Field of Classification Search
USPC .................................................. 607/45, 123
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| DE | 20010369 U1 | 8/2000 |
| EP | 0488512 B1 | 12/1996 |

(Continued)

OTHER PUBLICATIONS

Singh, Jagmeet P., et al. "Left Ventricular Lead Position and Clinical Outcome in the Multicenter Automatic Defibrillator Implantation Trial—Cardiac Resynchronization Therapy (MADIT-CRT) Trial." Circulation, 2011. 123:1159-1166.

(Continued)

*Primary Examiner* — Nicole F Lavert
(74) *Attorney, Agent, or Firm* — Faegre Baker Daniels LLP

(57) ABSTRACT

Various aspects of the present disclosure are directed toward apparatuses, systems, and methods that include a single pass implantable lead configured to be coupled to the implantable medical device and arranged to sense and pace the chambers of a patient's heart. The lead may include a proximal region having a plurality of electrodes, a distal region having at least one electrode, and an intermediate region therebetween. The system can sense and pace the right atrium, the left atrium, the right ventricle, and the left ventricle.

20 Claims, 9 Drawing Sheets

(51) Int. Cl.
  *A61N 1/365* (2006.01)
  *A61N 1/05* (2006.01)
  *A61N 1/362* (2006.01)
  *A61N 1/39* (2006.01)

(52) U.S. Cl.
  CPC ......... *A61N 1/3622* (2013.01); *A61N 1/3686* (2013.01); *A61N 1/36585* (2013.01); *A61N 1/3956* (2013.01)

(56) References Cited

U.S. PATENT DOCUMENTS

| | | |
|---|---|---|
| 4,122,294 A | 10/1978 | Frolov |
| RE30,366 E | 8/1980 | Rasor et al. |
| 4,332,259 A | 6/1982 | McCorkle |
| 4,399,818 A | 8/1983 | Money |
| 4,402,330 A | 9/1983 | Lindemans |
| 4,408,608 A | 10/1983 | Daly et al. |
| 4,458,677 A | 7/1984 | McCorkle et al. |
| 4,577,639 A | 3/1986 | Simon et al. |
| 4,592,359 A | 6/1986 | Galbraith |
| 4,665,925 A | 5/1987 | Millar |
| 4,889,128 A | 12/1989 | Millar |
| 4,928,688 A | 5/1990 | Mower |
| 4,932,407 A | 6/1990 | Williams |
| 4,957,111 A | 9/1990 | Millar |
| 4,958,632 A | 9/1990 | Duggan |
| 5,014,696 A | 5/1991 | Mehra |
| 5,076,272 A | 12/1991 | Ferek-Petric |
| 5,099,838 A | 3/1992 | Bardy |
| 5,117,824 A | 6/1992 | Keimel et al. |
| 5,144,960 A | 9/1992 | Mehra et al. |
| 5,165,403 A | 11/1992 | Mehra |
| 5,167,229 A | 12/1992 | Peckham et al. |
| 5,170,802 A | 12/1992 | Mehra |
| 5,224,491 A | 7/1993 | Mehra |
| 5,226,427 A | 7/1993 | Buckberg et al. |
| 5,265,601 A | 11/1993 | Mehra |
| 5,267,559 A | 12/1993 | Jin et al. |
| 5,277,231 A | 1/1994 | Dostalek |
| 5,279,291 A | 1/1994 | Adams et al. |
| 5,282,837 A | 2/1994 | Adams et al. |
| 5,304,139 A | 4/1994 | Adams et al. |
| 5,308,356 A | 5/1994 | Blackshear, Jr. et al. |
| 5,318,593 A | 6/1994 | Duggan |
| 5,331,966 A | 7/1994 | Bennett et al. |
| 5,350,404 A | 9/1994 | Adams et al. |
| 5,372,125 A | 12/1994 | Lyons |
| 5,387,233 A | 2/1995 | Alferness et al. |
| 5,405,374 A | 4/1995 | Stein |
| 5,409,469 A | 4/1995 | Schaerf |
| 5,411,524 A | 5/1995 | Rahul |
| 5,423,772 A | 6/1995 | Lurie et al. |
| 5,423,806 A | 6/1995 | Dale et al. |
| 5,431,683 A | 7/1995 | Bowald et al. |
| 5,433,729 A | 7/1995 | Adams et al. |
| 5,441,504 A | 8/1995 | Pohndorf et al. |
| 5,465,715 A | 11/1995 | Lyons |
| 5,466,254 A | 11/1995 | Helland |
| 5,476,498 A | 12/1995 | Ayers |
| 5,540,727 A | 7/1996 | Tockman et al. |
| 5,545,204 A | 8/1996 | Cammilli et al. |
| 5,549,581 A | 8/1996 | Lurie et al. |
| 5,549,642 A | 8/1996 | Min et al. |
| 5,578,069 A | 11/1996 | Miner, II |
| 5,609,621 A | 3/1997 | Bonner |
| 5,639,276 A | 6/1997 | Weinstock et al. |
| 5,643,231 A | 7/1997 | Lurie et al. |
| 5,645,569 A | 7/1997 | Ayers |
| 5,674,217 A | 10/1997 | Wahlstrom et al. |
| 5,676,687 A | 10/1997 | Ayers |
| 5,683,445 A | 11/1997 | Swoyer |
| 5,700,283 A | 12/1997 | Salo |
| 5,704,351 A | 1/1998 | Mortara et al. |
| 5,713,867 A | 2/1998 | Morris |
| 5,720,768 A | 2/1998 | Verboven-Nelissen |
| 5,722,963 A | 3/1998 | Lurie et al. |
| 5,744,038 A | 4/1998 | Cham |
| 5,755,761 A | 5/1998 | Obino |
| 5,755,766 A | 5/1998 | Chastain et al. |
| 5,759,202 A | 6/1998 | Schroeppel |
| 5,769,875 A | 6/1998 | Peckham et al. |
| 5,772,693 A | 6/1998 | Brownlee |
| 5,776,073 A | 7/1998 | Garfield et al. |
| 5,776,171 A | 7/1998 | Peckham et al. |
| 5,782,879 A | 7/1998 | Rosborough et al. |
| 5,800,465 A | 9/1998 | Thompson et al. |
| 5,800,495 A | 9/1998 | Machek et al. |
| 5,803,928 A | 9/1998 | Tockman et al. |
| 5,814,088 A | 9/1998 | Paul et al. |
| 5,824,032 A | 10/1998 | Belden |
| 5,843,117 A | 12/1998 | Alt et al. |
| 5,871,529 A | 2/1999 | Bartig et al. |
| 5,871,531 A | 2/1999 | Struble |
| 5,897,577 A | 4/1999 | Cinbis et al. |
| 5,899,929 A | 5/1999 | Thompson et al. |
| 5,902,324 A | 5/1999 | Thompson et al. |
| 5,913,887 A | 6/1999 | Michel |
| 5,922,014 A | 7/1999 | Warman et al. |
| 5,925,073 A | 7/1999 | Chastain et al. |
| 5,931,864 A | 8/1999 | Chastain et al. |
| 5,935,160 A | 8/1999 | Auricchio et al. |
| 5,954,758 A | 9/1999 | Peckham et al. |
| 5,954,761 A | 9/1999 | Machek et al. |
| 5,964,795 A | 10/1999 | McVenes et al. |
| 5,978,707 A | 11/1999 | Krig et al. |
| 5,983,138 A | 11/1999 | Kramer |
| 5,984,909 A | 11/1999 | Lurie et al. |
| 5,991,668 A | 11/1999 | Leinders et al. |
| 6,001,085 A | 12/1999 | Lurie et al. |
| 6,006,137 A | 12/1999 | Williams |
| 6,014,581 A | 1/2000 | Whayne et al. |
| 6,021,354 A | 2/2000 | Warman et al. |
| 6,026,328 A | 2/2000 | Peckham et al. |
| 6,027,462 A | 2/2000 | Greene et al. |
| 6,049,732 A | 4/2000 | Panescu et al. |
| 6,055,457 A | 4/2000 | Bonner |
| 6,070,100 A | 5/2000 | Bakels et al. |
| 6,070,104 A | 5/2000 | Hine et al. |
| RE36,765 E | 7/2000 | Mehra |
| 6,083,247 A | 7/2000 | Rutten et al. |
| 6,096,064 A | 8/2000 | Routh |
| 6,106,460 A | 8/2000 | Panescu et al. |
| 6,112,117 A | 8/2000 | Kenknight et al. |
| 6,115,626 A | 9/2000 | Whayne et al. |
| 6,122,553 A | 9/2000 | Ideker et al. |
| 6,129,750 A | 10/2000 | Tockman et al. |
| 6,132,456 A | 10/2000 | Sommer et al. |
| 6,148,233 A | 11/2000 | Owen et al. |
| 6,159,237 A | 12/2000 | Alt et al. |
| 6,161,029 A | 12/2000 | Spreigl et al. |
| 6,163,725 A | 12/2000 | Peckham et al. |
| 6,201,994 B1 | 3/2001 | Warman et al. |
| 6,219,579 B1 | 4/2001 | Bakels et al. |
| 6,223,082 B1 | 4/2001 | Bakels et al. |
| 6,238,420 B1 | 5/2001 | Bakels et al. |
| 6,295,475 B1 | 9/2001 | Morgan |
| 6,321,122 B1 | 11/2001 | Scheiner et al. |
| 6,321,123 B1 | 11/2001 | Morris et al. |
| 6,363,288 B1 | 3/2002 | Bush et al. |
| 6,377,856 B1 | 4/2002 | Carson |
| 6,397,109 B1 | 5/2002 | Cammilli et al. |
| 6,421,564 B1 | 7/2002 | Yerich et al. |
| 6,438,427 B1 | 8/2002 | Rexhausen et al. |
| 6,442,427 B1 | 8/2002 | Boute et al. |
| 6,445,958 B1 | 9/2002 | Machek et al. |
| 6,470,211 B1 | 10/2002 | Ideker et al. |
| 6,477,406 B1 | 11/2002 | Turcott |
| 6,490,489 B2 | 12/2002 | Bornzin et al. |
| 6,512,952 B2 | 1/2003 | Stahmann et al. |
| 6,539,260 B1 | 3/2003 | Schloss |
| 6,549,812 B1 | 4/2003 | Smits |
| 6,549,813 B2 | 4/2003 | Audoglio |
| 6,556,873 B1 | 4/2003 | Smits |

(56) References Cited

U.S. PATENT DOCUMENTS

| | | | |
|---|---|---|---|
| 6,584,362 B1 | 6/2003 | Scheiner et al. | |
| 6,628,988 B2 | 9/2003 | Kramer et al. | |
| 6,640,136 B1 | 10/2003 | Helland et al. | |
| 6,643,546 B2 | 11/2003 | Mathis et al. | |
| 6,650,945 B2 | 11/2003 | Helland et al. | |
| 6,654,639 B1 | 11/2003 | Lu | |
| 6,656,166 B2 | 12/2003 | Lurie et al. | |
| 6,658,289 B2 | 12/2003 | Helland | |
| 6,701,186 B2 | 3/2004 | Spinelli et al. | |
| 6,721,598 B1 | 4/2004 | Helland et al. | |
| 6,735,472 B2 | 5/2004 | Helland | |
| 6,745,081 B1 | 6/2004 | Helland et al. | |
| 6,748,268 B1 | 6/2004 | Helland et al. | |
| 6,754,530 B2 | 6/2004 | Bakels et al. | |
| 6,760,619 B1 | 7/2004 | Helland et al. | |
| 6,882,886 B1 | 4/2005 | Witte et al. | |
| 6,889,091 B2 | 5/2005 | Hine et al. | |
| 6,909,920 B2 | 6/2005 | Lokhoff et al. | |
| 6,936,040 B2 | 8/2005 | Kramm et al. | |
| 6,937,895 B1 | 8/2005 | Lu | |
| 6,961,621 B2 | 11/2005 | Krishnan et al. | |
| 6,985,776 B2 | 1/2006 | Kane et al. | |
| 6,988,007 B1 | 1/2006 | Morgan et al. | |
| 7,006,867 B1 | 2/2006 | Kroll | |
| 7,010,358 B1 | 3/2006 | Kroll et al. | |
| 7,027,861 B2 | 4/2006 | Thompson | |
| 7,054,687 B1 | 5/2006 | Andersen et al. | |
| 7,079,891 B1 | 7/2006 | Kroll | |
| 7,103,411 B1 | 9/2006 | Park et al. | |
| 7,139,610 B2 | 11/2006 | Ferek-Petric | |
| 7,139,614 B2 | 11/2006 | Scheiner et al. | |
| 7,142,919 B2 | 11/2006 | Hine et al. | |
| 7,149,579 B1 | 12/2006 | Koh et al. | |
| 7,181,284 B2 | 2/2007 | Burnes et al. | |
| 7,184,833 B2 | 2/2007 | Ganion et al. | |
| 7,203,543 B2 | 4/2007 | Meyer et al. | |
| 7,248,925 B2 | 7/2007 | Bruhns et al. | |
| 7,386,351 B2 | 6/2008 | Hine et al. | |
| 7,590,446 B1 | 9/2009 | Min et al. | |
| 7,657,323 B2 | 2/2010 | Kramm et al. | |
| 7,672,735 B2 | 3/2010 | Koop et al. | |
| 7,751,887 B1 | 7/2010 | Kroll et al. | |
| 7,765,015 B2 | 7/2010 | Johnson et al. | |
| 7,860,580 B2 | 12/2010 | Falk et al. | |
| 7,877,144 B2 | 1/2011 | Coles, et al. | |
| 7,925,346 B1 | 4/2011 | Go | |
| 7,979,124 B2 | 7/2011 | Meyer et al. | |
| 8,019,438 B2 | 9/2011 | Johnson et al. | |
| 8,041,426 B2 | 10/2011 | Fogoros et al. | |
| 8,155,756 B2 | 4/2012 | Yang et al. | |
| 8,224,463 B2 | 7/2012 | Worley | |
| 8,244,376 B2 | 8/2012 | Worley | |
| 8,306,622 B2 | 11/2012 | Arcot-Krishnamurthy et al. | |
| 8,340,767 B2 | 12/2012 | Liu et al. | |
| 8,380,308 B2 | 2/2013 | Rosenberg et al. | |
| 8,583,234 B1 | 11/2013 | Muller | |
| 8,594,792 B2 | 11/2013 | Liu et al. | |
| 8,670,824 B2 | 3/2014 | Anderson et al. | |
| 8,938,294 B2 | 1/2015 | Anderson et al. | |
| 9,162,066 B2 | 10/2015 | Hedberg et al. | |
| 9,233,251 B2 | 1/2016 | Rajan et al. | |
| 2003/0109914 A1 | 6/2003 | Westlund et al. | |
| 2005/0070981 A1 | 3/2005 | Verma | |
| 2005/0125041 A1 | 6/2005 | Min et al. | |
| 2005/0177218 A1 | 8/2005 | Kramm et al. | |
| 2005/0209649 A1 | 9/2005 | Ferek-Petric | |
| 2006/0047319 A1 | 3/2006 | Bruhns et al. | |
| 2006/0064150 A1 | 3/2006 | Heist et al. | |
| 2006/0247688 A1 | 11/2006 | Olson et al. | |
| 2006/0276869 A1 | 12/2006 | Worley | |
| 2007/0067008 A1 | 3/2007 | Scheiner et al. | |
| 2007/0093872 A1 | 4/2007 | Chirife et al. | |
| 2007/0142871 A1* | 6/2007 | Libbus | A61N 1/36114 607/45 |
| 2007/0179390 A1 | 8/2007 | Schecter | |
| 2007/0179541 A1 | 8/2007 | Prakash et al. | |
| 2007/0282413 A1 | 12/2007 | Tockman et al. | |
| 2007/0293923 A1 | 12/2007 | Soltis et al. | |
| 2008/0281368 A1* | 11/2008 | Bulkes | A61N 1/36114 607/4 |
| 2008/0300664 A1 | 12/2008 | Hine et al. | |
| 2008/0306567 A1 | 12/2008 | Park et al. | |
| 2009/0088827 A1 | 4/2009 | Tockman et al. | |
| 2009/0216291 A1 | 8/2009 | Holmström et al. | |
| 2009/0299423 A1 | 12/2009 | Min | |
| 2010/0145405 A1 | 6/2010 | Min et al. | |
| 2011/0015714 A1 | 1/2011 | Atkinson et al. | |
| 2011/0016820 A1 | 1/2011 | Greeff | |
| 2011/0022106 A1 | 1/2011 | Min | |
| 2011/0022110 A1 | 1/2011 | Min | |
| 2011/0022112 A1 | 1/2011 | Min | |
| 2011/0054560 A1 | 3/2011 | Rosenberg et al. | |
| 2011/0071609 A1 | 3/2011 | Zarembo et al. | |
| 2011/0160792 A1 | 6/2011 | Fishel | |
| 2011/0160820 A1 | 6/2011 | Jackson et al. | |
| 2011/0230922 A1 | 9/2011 | Fishel | |
| 2012/0153967 A1* | 6/2012 | Koop | A61N 1/371 324/615 |
| 2013/0030512 A1 | 1/2013 | McCready et al. | |
| 2013/0184777 A1* | 7/2013 | Hellman | A61B 5/0452 607/28 |
| 2015/0148645 A1 | 5/2015 | Regnier et al. | |
| 2017/0001001 A1 | 1/2017 | Liu et al. | |

FOREIGN PATENT DOCUMENTS

| | | |
|---|---|---|
| EP | 0951920 A2 | 10/1999 |
| EP | 1013303 A1 | 6/2000 |
| EP | 1627660 A1 | 2/2006 |
| EP | 1501597 B1 | 7/2008 |
| EP | 2075033 B1 | 7/2015 |
| JP | 2011502021 A | 1/2011 |
| JP | 2012523301 A | 10/2012 |
| JP | 2012531288 A | 12/2012 |
| JP | 2016508767 A | 3/2016 |
| WO | 199913941 A1 | 3/1999 |
| WO | WO03090861 A1 | 11/2003 |
| WO | 2007089176 A1 | 8/2007 |

OTHER PUBLICATIONS

International Search Report and Written Opinion issued in PCT/US2016/062929, dated Feb. 8, 2017, 11 pages.

Bacik, Bradley and Corbisiero, Raffaele, Adaptive Bi-Atrial Pacing Improves the Maintenance of Sinus Rhythm. PACE, 30:492-497, Apr. 2007.

Gaubert, Claude et al. Permanent Left Atrial Pacing with a Specifically Designed Coronary Sinus Lead. PACE, 20:2755-2764, Nov. 1997.

De Simone, Antonio, et al. Dynamic and Dual-Site Atrial Pacing in the Prevention of Atrial Fibrillation: The Stimuloazione Atrial Dinamica Multisito (STADIM) Study. PACE 30:S71-S74, Jan. 2007, Supplement 1.

International Search Report and Written Opinion issued in PCT/US2016/040591 dated Sep. 30, 2016, 11 pages.

Kramer, David H., et al. Permanent Pervenous Atrial Pacing from the Coronary Vein. Circulation, XLII:427-436, Mar. 4, 2015.

Moss, Arthur J., et al. Permanent Pervenous Atrial Pacing From the Coronary Vein Long-Term Follow-Up. Circulation. XLIX:222-225, Feb. 1974.

Ouali, Sana. Effective Long-Term Left Atrial Pacing Using Regular Screw-In Leads Implanted Within the Coronary Sinus, PACE, 26:1873-1877, Sep. 2003.

International Preliminary Report on Patentability issued in PCT/US2016/040591, dated Jan. 11, 2018, 8 pages.

International Preliminary Report on Patentability issued in PCT/US2016/062929, dated May 31, 2018, 8 pages.

* cited by examiner

SINGLE PASS CORONARY VENOUS LEAD FOR MULTIPLE CHAMBER SENSE AND PACE

CROSS-REFERENCE TO RELATED APPLICATION

This application claims priority to Provisional Application No. 62/258,392, filed Nov. 20, 2015, which is herein incorporated by reference in its entirety.

TECHNICAL FIELD

The present invention relates to medical devices and methods for stimulating/sensing a patient's heart. More specifically, the invention relates to devices and methods for stimulating/sensing the left atrium, right atrium, left ventricle, and right ventricle of the heart in a minimally-invasive manner.

BACKGROUND

Implantable medical devices, such as electrical stimulators or sensors, are used in a variety of therapeutic applications. In some implantable medical devices, an electrical stimulator or sensor delivers electrical pulses to a target tissue site within a patient with the aid of one or more medical leads. The medical leads are coupled to the implantable medical device at one end while the other end carrying electrodes is placed at the target tissue site. Historically, different target tissue sites have been selected for different therapeutic applications. The electrodes may be used in stimulating and/or sensing applications.

SUMMARY

In Example 1, a method of pacing of a patient's heart using a single pass implantable lead, the method comprising: positioning a proximal region of the single pass implantable lead such that one or more proximal electrodes are positioned in the coronary sinus and/or great cardiac vein of the patient's heart; positioning a distal region of the single pass implantable lead in a coronary vein of the patient's heart such that one or more distal electrodes are situated adjacent to an intraventricular septum of the patient's heart; electrically connecting the single pass implantable lead to a pulse generator or implantable medical device; sensing an atrial and a ventricular signal of the patient's heart via at least one of the proximal electrodes and the distal electrodes; selecting at least one distal electrode having a right ventricle and left ventricle pacing threshold near a designated pacing threshold; transmitting a pacing signal to the patient's heart via the selected at least one distal electrode, the transmitted pacing signal causing a desired contraction of both the right ventricle and the left ventricle.

In Example 1, an implantable medical system comprising an implantable lead and an implantable pulse generator. The implantable lead includes lead body defining a proximal region and a distal region, the proximal region including a plurality of proximal electrodes positioned on the lead body so that at least one of the proximal electrodes can be positioned in a coronary sinus or great cardiac vein of a patient's heart, the distal region including a plurality of distal electrodes disposed on the lead body so that at least one of the distal electrodes can be positioned within a coronary vein proximate an intraventricular septum of the patient's heart. The implantable pulse generator is configured to be electrically coupled to the implantable lead, and includes electronic circuitry configured to cause a pacing signal to be delivered to the patient's heart via at least one selected distal electrode of the plurality of distal electrodes. The implantable medical system is configured so that the pacing signal delivered via the at least one selected distal electrode can capture both a right ventricle and a left ventricle of the patient's heart, wherein the at least one selected distal electrode is selected based on right and left ventricular pacing thresholds associated therewith.

In Example 2, the implantable medical system of Example 1, wherein the distal region of the implantable lead is configured to be positioned within an anterior coronary vein of the patient's heart.

In Example 3, the implantable medical system of Example 1 or 2, wherein the right and left ventricular pacing thresholds associated with the at least one selected distal electrode are below a designated maximum pacing threshold value.

In Example 4, the implantable medical system of any of the preceding Examples, wherein the implantable lead and the implantable pulse generator are configured such that a first one of the plurality of distal electrodes has first right and left ventricular pacing thresholds associated therewith, and a second one of the plurality of distal electrodes has second right and left ventricular pacing thresholds associated therewith, and wherein the at least one selected distal electrode is the first one of the plurality of distal electrodes or the second one of the plurality of distal electrodes.

In Example 5, the implantable medical system of any of the preceding Examples, wherein the at least one selected distal electrode is operable as a right and left ventricular pacing electrode.

In Example 6, the implantable medical system of any of the preceding Examples, wherein at least one distal electrode is operable as a right and left ventricular sensing electrode.

In Example 7, the implantable medical system of any of Examples 4-6, wherein the at least one selected distal electrodes includes the first one of the plurality of distal electrodes and the second one of the plurality of distal electrodes being configured so as to be operable, in combination, to pace the right ventricle and a left ventricle of the patient's heart.

In Example 8, the implantable medical system of any of Examples 4-7, wherein the implantable lead and the implantable pulse generator are configured such that the first one of the plurality of distal electrodes and the second one of said plurality of distal electrodes, in combination, have associated therewith right and left ventricular pacing thresholds that are less than the right and left ventricular pacing thresholds associated with the first and the second one of the plurality of distal electrodes, individually.

In Example 9, the implantable medical system of any of the preceding Examples, wherein a first group of the plurality of proximal electrodes is disposed along the implantable lead distal to the one or more proximal electrodes disposed so as to be positionable in the coronary sinus and/or the great cardiac vein of the patient's heart, and wherein a first one of the first group of the plurality of proximal electrodes has a first left atrial pacing threshold associated therewith, and wherein a second one of the first group of the plurality of proximal electrodes has a second left atrial pacing threshold associated therewith.

In Example 10, the implantable medical system of Example 9, wherein the second left atrial pacing threshold exceeds the first left atrial pacing threshold.

In Example 11, the implantable medical system of Example 9 or 10, wherein the first one of the first group of the plurality of proximal electrodes is operable as a left atrial pacing electrode.

In Example 12, the implantable medical system of any of Examples 9-11, wherein the first one of the first group of the plurality of proximal electrodes is operable as a left atrial sensing electrode.

In Example 13, the implantable system of any of Examples 9-11, wherein the second one of the first group of the plurality of proximal electrodes is operable as a left atrial sensing electrode.

In Example 14, the implantable system of Example 9, wherein the first one of the first group of the plurality of proximal electrodes and the second one of the first group of the plurality of proximal electrodes are operable, in combination, to pace the left atrium of the patient's heart.

In Example 15, the implantable system of any of the preceding Examples, wherein the pulse generator is configured to deliver the pacing signal for treating bradyarrhythmia or tachyarrhythmia.

In Example 16, a method of pacing a patient's heart using an implantable lead having a proximal region including at least one proximal electrode positioned in a coronary sinus or great cardiac vein of the patient's heart and a distal region positioned in a coronary vein of the patient's heart such that at least one of a plurality of distal electrodes is situated proximate an intraventricular septum of the patient's heart. The method comprises sensing an atrial and a ventricular signal of the patient's heart via at least one of the proximal electrodes and one of the distal electrodes, respectively, and determining a pacing threshold associated with each of the plurality of distal electrodes. The method further comprises selecting at least one of the plurality of distal electrodes that have associated therewith right and left ventricular pacing thresholds, and delivering a pacing signal to the patient's heart via the selected at least one distal electrode, the transmitted pacing signal causing a desired contraction of both the right ventricle and the left ventricle.

In Example 17, the method of Example 16, wherein the distal region of the implantable lead is positioned within an anterior coronary vein.

In Example 18, the method Example 16, wherein selecting the at least one of the plurality of distal electrodes includes selecting at least one distal electrode having associated therewith right and left ventricular pacing thresholds below a designated maximum pacing threshold value.

In Example 19, the method of Example 16, wherein determining the pacing threshold associated with each of the plurality of distal electrodes further comprises determining a right and left ventricle pacing threshold associated with a first one of the plurality of distal electrodes and determining a right and left ventricle pacing threshold associated with a second one of the plurality of distal electrodes.

In Example 20, the method of Example 19, wherein the first one of said plurality of distal electrodes has associated therewith first right and left ventricular pacing thresholds and the second one of the plurality of distal electrodes has associated therewith second right and left ventricular pacing thresholds, the second right and left ventricular pacing thresholds exceeding said first right and left ventricular pacing thresholds.

In Example 21, the method of Example 16, further comprising selecting the first one of the plurality of distal electrodes as a right and left ventricular pacing electrode.

In Example 22, the method of Example 21, further comprising selecting the first one of the plurality of distal electrodes or the second one of the plurality of distal electrodes as a right and left ventricular sensing electrode.

In Example 23, the method of Example 16, further comprising selecting the first one of the plurality of distal electrodes and the second one of the plurality of distal electrodes to operate, in combination, to pace a right ventricle and a left ventricle of the patient's heart.

In Example 24, the method Example 23, wherein selecting the first one of the plurality of distal electrodes and the second one of the plurality of distal electrodes to operate, in combination, to pace a right ventricle and a left ventricle of the patient's heart is based on left and right ventricular pacing thresholds associated with the first and said second ones of the plurality of distal electrodes, in combination, being less than the right and left ventricular pacing thresholds of the first and the second one of the plurality of distal electrodes, individually.

In Example 25, the method of Example 16, wherein a first group of the plurality of proximal electrodes is disposed along the implantable lead distal to the one or more proximal electrodes positioned in the coronary sinus or the great cardiac vein of the patient's heart, and wherein the method further comprises determining a left atrial pacing threshold associated with a first one of the first group of the plurality of proximal electrodes, and determining a left atrial pacing threshold associated with a second one of said the first group of the plurality of proximal electrodes, wherein the second determined left atrial pacing threshold exceeds the first determined left atrial pacing threshold, and selecting the first one of said the first group of the plurality of proximal electrodes as a left atrial pacing electrode based on the second determined left atrial pacing threshold exceeding the first determined left atrial pacing threshold.

In Example 26, the method of Example 25, further comprising selecting the first one of the first group of the plurality of proximal electrodes or the second one of the first group of the plurality of proximal electrodes as a left atrial sensing electrode.

In Example 27, the method of Example 25, further comprising selecting the first one of the first group of the plurality of proximal electrodes and the second one of the first group of the plurality of proximal electrodes to operate, in combination, to pace the left atrium of the patient's heart.

In Example 28, a method of inserting an implantable lead into a patient's heart, the implantable lead having a proximal region including a plurality of proximal electrodes and a distal region including at least one distal electrode. The method comprises inserting the implantable lead into the patient's heart via a superior vena cava or an inferior vena cava, and positioning the implantable lead such that at least a portion of the proximal region of the single pass implantable lead is positioned within a coronary sinus of the patient's heart and at least a portion of the distal region of the single pass implantable lead is positioned within an anterior coronary vein, with the at least one distal electrode being positioned adjacent to an intraventricular septum of the patient's heart. The method further comprises electrically connecting the single pass implantable lead to a pulse generator or an implantable medical device, selecting a first proximal electrode from the plurality of proximal electrodes to operate as a right atrial pacing electrode based on a measured right atrial pacing threshold associated with the first proximal electrode, and selecting a second proximal electrode from the plurality of proximal electrodes to operate as a left atrial pacing electrode based on a measured left atrial pacing threshold associated with the second proximal electrode. The method further comprises selecting a first distal electrode from the at least one distal electrode to operate as a right ventricular and left ventricular pacing electrode based on measured right and left ventricular pacing thresholds associated with the first distal electrode.

In Example 29, the method of Example 28, wherein the first proximal electrode is positioned proximate a coronary sinus ostium within the coronary sinus, and the second proximal electrode is positioned within the coronary sinus or a great cardiac vein and adjacent a myocardium of a left atrium.

In Example 30, the method of Example 29, wherein the plurality of proximal electrodes includes at least a third proximal electrode positioned proximate the second proximal electrode and wherein the second proximal electrode is selected based on the measured left atrial pacing threshold associated with the second proximal electrode being less than a measured left atrial pacing threshold associated with the third proximal electrode.

In Example 31, the method of Example 30, wherein the third proximal electrode is designated as a left atrial sensing electrode.

In Example 32, the method of Example 30, wherein the third proximal electrode is also selected as a left atrial pacing electrode such that the second and the third proximal electrodes operate together to deliver a pacing signal to the patient's heart, wherein a measured left atrial pacing threshold of the second and third proximal electrodes, in combination, being less than the measure left atrial pacing threshold of the second and third proximal electrodes individually.

In Example 33, the method of Example 28, wherein the plurality of proximal electrodes includes at least a fourth proximal electrode positioned along the single pass lead proximal of the first proximal electrode, the fourth proximal electrode being positioned within a right atrium and being designated as a right atrial sensing electrode.

In Example 34, a method of performing biventricular pacing of a patient's heart using an implantable lead. The method comprises positioning a proximal region of the implantable lead such that one or more proximal electrodes are positioned in a coronary sinus or the great cardiac vein of the patient's heart, and positioning a distal region of the implantable lead in an anterior coronary vein of the patient's heart such that one or more distal electrodes are situated adjacent to an intraventricular septum of the patient's heart. The method further comprises sensing an atrial and a ventricular signal of the patient's heart via one or more of the proximal electrodes and distal electrodes, selecting at least one distal electrode having associated therewith right and left ventricular pacing thresholds below a designated pacing threshold, and delivering, via a pulse generator coupled to the implantable lead, a pacing signal to the patient's heart via the selected at least one distal electrode, the delivered pacing signal causing a desired contraction of both the right ventricle and the left ventricle.

In Example 35, the method of Example 34, wherein the implantable lead includes a plurality of proximal electrodes, a first one of the proximal electrodes being the proximal electrode positioned proximate the coronary sinus ostium of the patient's heart, the first one of the proximal electrodes being operable to sense and pace at least the right atrium of the patient's heart.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
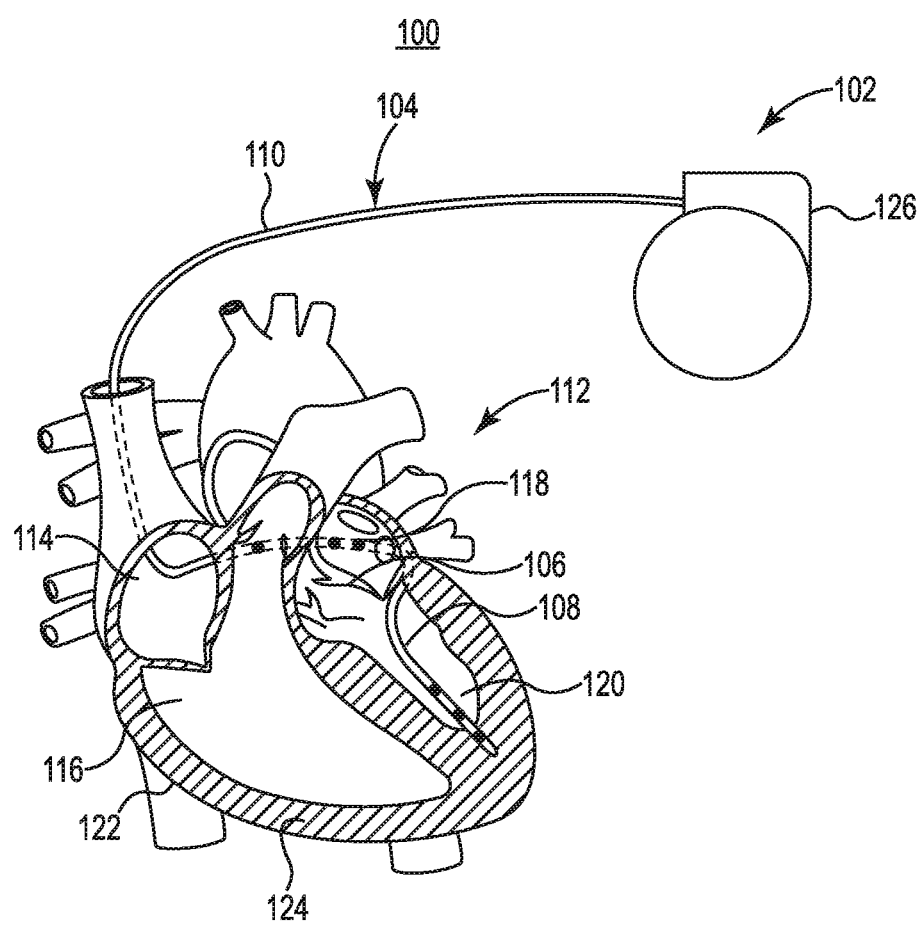
FIG. 1 is a schematic view of an implantable system including an exemplary implantable medical device and an implantable lead in accordance with embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an implantable system 100 including an exemplary implantable medical device 102 and an implantable lead 104 in accordance with embodiments of the present disclosure. As shown, the system 100 includes the implantable medical device 102 and the implantable lead 104. As indicated in FIG. 1, the implantable lead 104 includes a proximal end, indicated generally at 106 and a distal end, indicated generally at 108. Further, the implantable lead 104 may include a flexible lead body 110. As shown in FIG. 1, the heart 112 includes a right atrium 114, a right ventricle 116, a left atrium 118, a left ventricle 120, and a tricuspid valve 128. It can be seen that the heart 112 includes an epicardium 122 covering the myocardium 124.

The implantable medical device 102 may be implanted subcutaneously within an implantation location or pocket in the patient's chest or abdomen. The implantable medical device 102 may be any implantable medical device known in the art or later developed, for detecting a cardiac condition of a patient and/or delivering an electrical therapeutic stimulus to the patient. In various embodiments, the implantable medical device 102 is a pacemaker, an implantable cardioverter/defibrillator (ICD), a cardiac resynchronization (CRT) device configured for pacing, and/or includes combinations of pacing, CRT, and defibrillation capabilities. In embodiments in which the medical device 102 includes defibrillation capabilities, the implantable lead 104 may include one or more high voltage defibrillation coil electrodes (not shown). In addition, or alternatively, the system 100 may utilize a separate right ventricular lead (not shown), which may be of any design, now known or later developed, having one or more high voltage defibrillation coil electrodes for delivering high voltage defibrillation shocks. For example, a separate right ventricular lead (not shown), may be place in a patient's right ventricle such that it is one or more high voltage defibrillation coil electrodes are operable to deliver one or more high voltage defibrillation shocks to the patient's heart tissue.

In one embodiment, the implantable medical device 102 is capable of providing defibrillation therapy and may utilize a subcutaneously implantable lead (not shown) in addition with the implantable lead 104, which as discussed previously herein, may also include one or more high voltage defibrillation coil electrodes.

The implantable medical device 102 may include a header 126. The header 126 may include one or more connector port (not shown) to couple the implantable lead 104 to the implantable medical device 102. The connector port of the header electrically and physically contacts a connector assembly (not shown) of the implantable lead 104. The header 126 is attached to a hermetically sealed enclosure that contains a battery, electronic circuitry, and other components known to those skilled in the art. Electrical contacts (not shown) in the header 126 are any type known to those skilled in the art that are electrically connected via feedthroughs (not shown) mounted to extend through the hermetically sealed enclosure in order to electrically couple the implantable lead 104 with implantable medical device 102. Exemplary connectors that may be used in conjunction with the implantable medical device 102 can include, but are not limited to, a quadripolar (e.g., IS-4 or similar) connector, a bipolar (e.g., IS-1 or similar) connector, or an IS-1 plus IS-4, or an IS-4 plus IS-4 connected by a Y adaptor, or in embodiments in which the medical device 102 has defibrillation capabilities, one or more DF-1 and/or DF-4 connectors. In one embodiment, the connector may be an 8 terminal ring connector. The electronic circuitry, included with the header 126 and while not shown, is configured to as a detection/energy delivery system configured to receive cardiac rhythm signals from the electrode(s) (not shown) provided with the implantable lead 104.

The lead body 110 of the lead 104 can be made from any flexible, biocompatible material suitable for lead construction. In various embodiments, the lead body 110 is made from a flexible, electrically insulative material. In one embodiment, the lead body 110 is made from silicone. In another embodiment, the lead body 110 is made from polyurethane. In various embodiments, respective segments of the lead body 110 are made from different materials, so as to tailor the lead body 110 characteristics to its intended clinical and operating environments. In various embodiments, proximal and distal ends of the lead body 110 are made from different materials selected to provide desired functionalities.

The implantable lead 104 may be a bipolar pacing lead including a single terminal pin and ring electrode. In addition, the implantable lead 104 may be a multi-polar left side lead with two or more low-voltage electrodes. In various embodiments, the implantable lead 104 may include one or more ventricular electrodes, one or more right atrium (RA) electrodes, and one or more left atrium (LA) electrodes. The lead 104 may include electrodes for sensing the electrical activity of the heart 112 and/or applying a stimulating pulse to the right atrium 114, the left atrium 118, the right ventricle 116, and/or the left ventricle 120. The implantable lead 104 may include sensing capabilities (e.g., a pressure sensing/pacing lead with a quadripolar type connector). More specifically, during therapy delivery, the circuitry provided with the header 126 controls electrodes provided with the implantable lead 104 to detect and/or measuring various physiological parameters. Example parameters that can be detected and/or measured include, but are not limited to, transthoracic impedance, respiratory rate, minute ventilation, heart rate, heart rate variability, cardiac dyssynchrony, activity, posture, blood chemistry, O2 saturation, heart sounds, wall stress, strain, hypertrophy, inter-electrode impedance, electrical timing delays (e.g., RA-LA interval, AV interval, Q-LV interval, etc.), cardiac pressure (e.g., RA and/or coronary venous pressure), cardiac output, temperature, depolarization amplitudes, and depolarization timing. Information from one or more of these physiological parameters may be used to adjust operating parameters such as the amplitude, timing, and/or pulse width of the stimulus energy delivered to the lead 104 from the implantable medical device 102.

In various embodiments, if the single pass implantable lead is implanted in the lateral or posterior vein, the single pass implantable lead can provide CRT therapy for a patient displaying an RV-LV asynchronous ventricular contraction. Accordingly, the versatility of the single pass implantable lead may be adapted for bradycardia therapy or tachycardia therapy (e.g., via antitachycardia pacing) in addition to or in lieu of CRT therapy.

Figure 2:
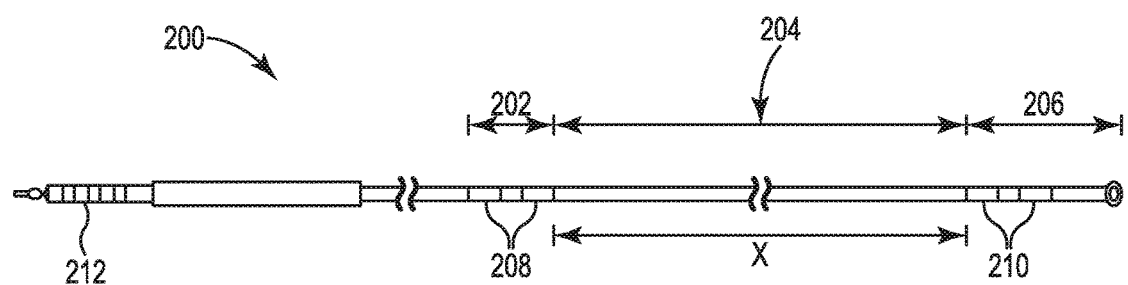
FIG. 2 is a schematic view of an exemplary single pass implantable lead in accordance with embodiments of the present disclosure.

FIG. 2 is a schematic view of an exemplary single pass implantable lead 200 in accordance with embodiments of the present disclosure. In certain instances and as discussed in further detail below, the single pass implantable lead 200 may provide pacing to the left atrium (LA), the right atrium (RA), the left ventricle (LV), and/or the right ventricle (RV) of a patient. Such a lead obviates the need for a separate pacing lead in the right atrium (RA) and/or the right ventricle (RV). The single pass implantable lead 200 includes a proximal region 202, a distal region 206, and an intermediate region 204 between the proximal region 202 and the distal region 206. The proximal region 202 includes one or more proximal electrodes 208, and the distal region 206 includes one or more distal electrodes 210. The one or more proximal electrodes 208 and/or the one or more distal electrodes 210 may be configured to sense and/or pace a patient's heart. In one embodiment, the proximal region 202 includes two or more proximal electrodes 208. In one embodiment, the distal region 206 includes one or more distal electrodes 210. In addition, the proximal region 202 may have a greater thickness (not shown) than the thickness of the distal region 206. In certain instances, the proximal region 202 may be thicker to enhance contact of the one or more proximal electrodes 208 against a vessel wall. As is shown in FIG. 2, the proximal region 202 includes two proximal electrodes 208 and the distal region 206 includes two distal electrodes 210. In certain instances, multiple proximal electrodes 208 may be coupled to a common conductor. As a result, the multiple proximal electrodes 208 may be configured to sense or pace simultaneously or in a coordinated manner. In addition, multiple distal electrodes 210 may be coupled to a common conductor, and thus may be configured to sense or pace simultaneously or in a coordinated manner. The proximal electrodes 208 and distal electrodes 210 may be connected to different conductors.

Due to the spacing between the proximal region 202 and the distal region 206, the proximal electrodes 208 and the distal electrodes 210 may sense and/or pace different locations of the heart. For example, the distance "X" provided by the intermediate region 204, separating the proximal electrodes 208 and the distal electrodes 210, may be provided such that the proximal electrodes 208 are positionable in the right atrium at the coronary sinus ostium (CS OS) 308 and in the coronary sinus (CS) or the great cardiac vein (GCV). In one embodiment, the distance "X" provided by the intermediate region 204, separating the proximal electrodes 208 and the distal electrodes 210, may be provided such that the distal electrodes 210 are positionable in the coronary branch, over the septum between the left and right ventricles, in close proximity to the mid-to-apex of the heart. In some embodiments, the distance "X" may be between 2 cm and 15 cm. As a result, the proximal electrodes 208 may be configured to sense and/or pace the left atrium and the right atrium of the patient, and the distal electrodes 210 may be configured to sense and/or pace the left ventricle and the right ventricle of the patient. Although not shown, the single pass implantable lead 200 may be coupled to an implantable medical device via a connector 212.

Figure 3A:
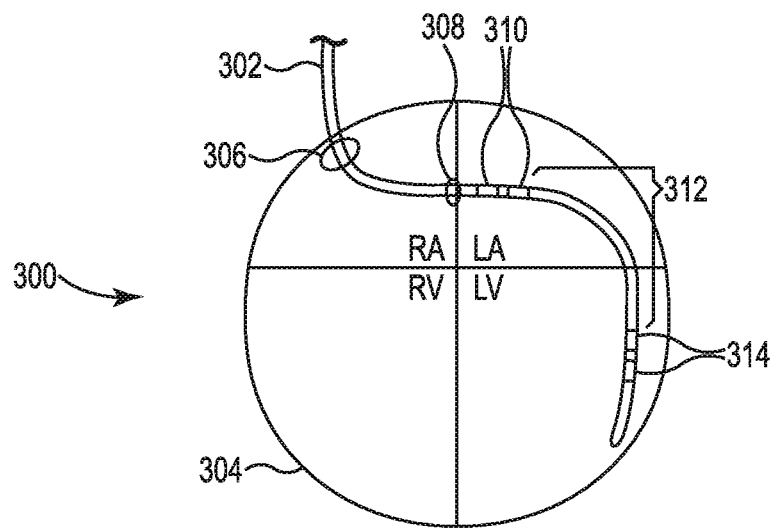
FIG. 3A is an illustration of an exemplary placement of a single pass implantable lead in a patient's heart in accordance with embodiments of the present disclosure.

FIG. 3A is an illustration 300 of an exemplary embodiment, illustrating placement of a single pass implantable lead 302 in a patient's heart 304 in accordance with certain embodiments of the present disclosure. The illustration 300 shows the heart 304 broken into the four quadrants: right atrium (RA), right ventricle (RV), left atrium (LA), and left ventricle (LV). The single pass implantable lead 302 is shown entering the heart 304 via the superior vena cava 306, and routed epicardially around the LA through the coronary sinus ostium (CS OS) 308. In certain other embodiments, the single pass implantable lead 302 may enter or be routed through the inferior vena cava. A region of the single pass implantable lead 302 around the LA includes one or more proximal electrodes 310. In one embodiment, the one or more proximal electrodes 310 may be anchored in and/or contact the great cardiac vein (GCV) or coronary sinus (CS) in a way to be adjacent to the myocardium of the LA or may be anchored in and/or contact the myocardial sleeve of the CS and GCV. From this position, the single pass implantable lead 302 is further routed through the vasculature of the heart 304 to a position around the LV. The region of the single pass implantable lead 302 that is routed between the LA electrodes (310) and the LV electrodes (314) is an intermediate portion 312. A region of the single pass implantable lead 302 on the LV includes one or more distal electrodes 314. The one or more distal electrodes 314 may be positioned, for example in the coronary branch of the heart 304.

Figure 3B:
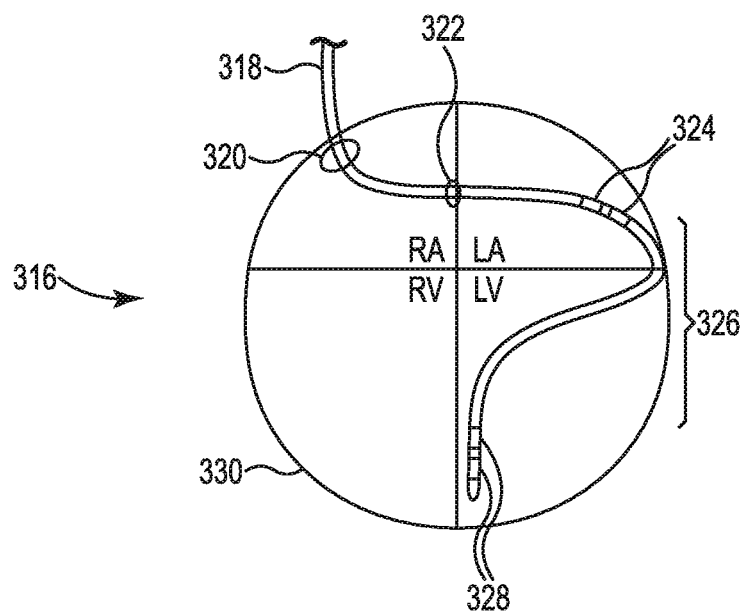
FIG. 3B is an illustration of another exemplary placement of a single pass implantable lead in a patient's heart in accordance with embodiments of the present disclosure.

FIG. 3B is an illustration 316 of another exemplary embodiment, illustrating placement of a single pass implantable lead in a patient's heart 330. Similar to the illustration 300 shown in FIG. 3A, the illustration 316 shows the heart 330 broken into the four quadrants: right atrium (RA), right ventricle (RV), left atrium (LA), and left ventricle (LV). In this illustrated example, the single pass implantable lead 318 enters the heart 330 via the superior vena cava 320, and is routed epicardially around the LA through the coronary sinus ostium (CS OS) 322. A region of the single pass implantable lead 318 on the LA includes one or more proximal electrodes 324, which may be anchored in the great cardiac vein (GCV) or coronary sinus (CS) in a way to be adjacent to the myocardium of the LA or may be anchored in and/or contact the myocardial sleeve of the CS and GCV. From this position, the single pass implantable lead 318 may be further routed through the vasculature of the heart 330 to a position on or adjacent the LV. In the schematic shown in FIG. 3B, the single pass implantable lead 318 is routed further within the vasculature toward the interventricular septum between the LV and right ventricle (RV). An intermediate portion 326 provides a sufficient length to allow for this routing. In addition, a region of the single pass implantable lead 318 on or adjacent the LV includes one or more distal electrodes 328. The one or more distal electrodes 328 may be positioned, for example in the anterior vein adjacent the ventricular septum of the heart 330.

Figure 3C:
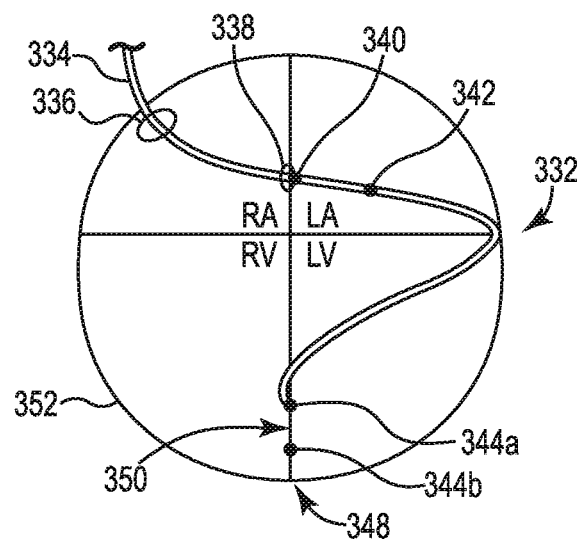
FIG. 3C is an illustration of another exemplary placement of a single pass implantable lead in a patient's heart in accordance with embodiments of the present disclosure.

FIG. 3C is an illustration 332 of an exemplary embodiment, illustrating placement of a single pass implantable lead 334 in a patient's heart 352 and utilized to treat certain types of cardiac conditions, such as bradyarrythmias and the like. The illustration 332 shows the heart 352 broken into the four quadrants: right atrium (RA), right ventricle (RV), left atrium (LA), and left ventricle (LV). The single pass implantable lead 334 is shown entering the heart 352 via the superior vena cava 336, and routed epicardially around the LA through the coronary sinus ostium (CS OS) 338. A region of the single pass implantable lead 334 around the LA includes two or more proximal electrodes 340 and 342. In one embodiment, proximal electrode 340 may be anchored in the coronary sinus (CS) at the coronary sinus ostium (CS OS) 338 and may operate to sense and/or pace the right atrium (RA). In one embodiment, electrode 342 may be anchored in and/or contact the great cardiac vein (GCV) or coronary sinus (CS) in a way to be adjacent to the myocardium of the left atrium (LA) or may be anchored in and/or contact the myocardial sleeve of the CS and GCV and may operate to sense and/or pace the left atrium (LA). From this position, the single pass implantable lead 334 is further routed through the vasculature of the heart 352 such that the one or more distal electrodes 344 are positioned above the septum 350 between the left ventricle (LV) and the right ventricle (RV). In one such embodiment, the distal electrodes 344 are positioned along the septum 350 in close proximity to the mid-to-apex 348 of the heart 352. In another such embodiment, the distal electrodes 344 are positioned along the septum 350 of the heart 348 at a more proximal location relative to the mid-to-apex 348 of the heart 352. The one or more distal electrodes 344 may be positioned, for example in the coronary branch of the heart 352 and may operate to sense and/or pace both the left ventricle (LV) and the right ventricle (RV). The region of the single pass implantable lead 334 that is routed between the proximal electrodes (340 and 342) and the distal electrodes (344) is an intermediate portion (see discussion above).

Figure 3D:
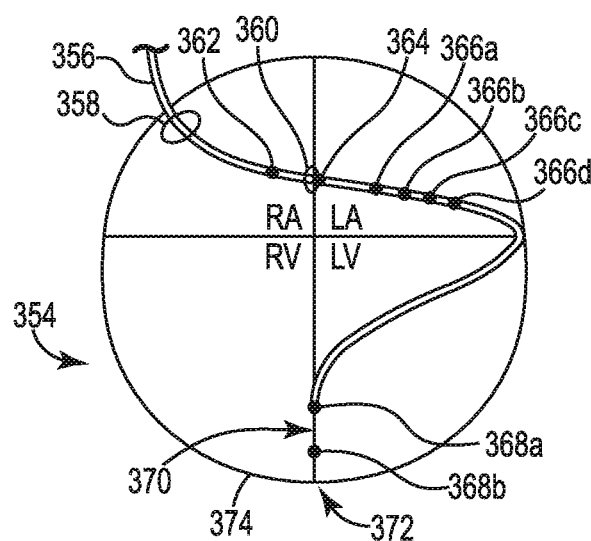
FIG. 3D is an illustration of another exemplary placement of a single pass implantable lead in a patient's heart in accordance with embodiments of the present disclosure.

FIG. 3D is an illustration 354 of an exemplary embodiment, illustrating placement of a single pass implantable lead 356 in a patient's heart 374 and utilized to treat certain types of cardiac conditions, such as bradyarrythmias and the like. The illustration 354 shows the heart 374 broken into the four quadrants: right atrium (RA), right ventricle (RV), left atrium (LA), and left ventricle (LV). The single pass implantable lead 356 is shown entering the heart 374 via the superior vena cava 358, and routed epicardially around the left atrium (LA) through the coronary sinus ostium (CS OS) 360. A region of the single pass implantable lead 356 around the left atrium (LA) includes a plurality of proximal electrodes 362, 364, and 366. In one embodiment, proximal electrode 362 is positioned within the right atrium (RA) of the patient's heart. In one embodiment, proximal electrode 362 is a floating electrode and operates to sense the right atrium (RA). In one embodiment, proximal electrode 364 may be anchored in the coronary sinus (CS) at the coronary sinus ostium (CS OS) 360 and may operate to sense and/or pace the right atrium (RA). In certain other embodiments, proximal electrode 364 may be a floating electrode floating in the CS. Additionally, in one embodiment, proximal electrodes 366 may be anchored in and/or contact the great cardiac vein (GCV) or coronary sinus (CS) in a way to be adjacent to the myocardium of the left atrium (LA) or may be anchored in and/or contact the myocardial sleeve of the CS and GCV, and may operate to sense and/or pace the left atrium (LA). In certain other embodiments, one or more of proximal electrodes 366 may be floating within the GCV. In various embodiments, electrodes 366a, 366b, 366c, and 366d (or any other suitable electrodes at any of the other locations along the single pass implantable lead) may be located on a shape of a bias, as discussed herein, to increase the chance of left atrium (LA) myocardial wall contact and lower the pacing threshold (as discussed herein). Additionally and/or alternatively, electrodes 366a, 366b, 366c, and 366d (or any other suitable electrodes at any of the other locations along the single pass implantable lead) may be connected with one conductor or multiple conductors to increase the chance of left atrium (LA) myocardial wall contact and lower the pacing threshold (as discussed herein).

From this position, the single pass implantable lead 356 is further routed through the vasculature of the heart 374 such that the one or more distal electrodes 368 are positioned above the septum 370 between the left ventricle (LV) and the right ventricle (RV) in close proximity to the mid-to-apex of the heart 372. The one or more distal electrodes 368 may be positioned, for example in the coronary branch of the heart 374 and operate to sense and/or pace both the left ventricle (LV) and the right ventricle (RV). The region of the single pass implantable lead 356 that is routed between the proximal electrodes (362, 364, and 366) and the distal electrodes (368) is an intermediate portion (see discussion above).

Figure 3E:
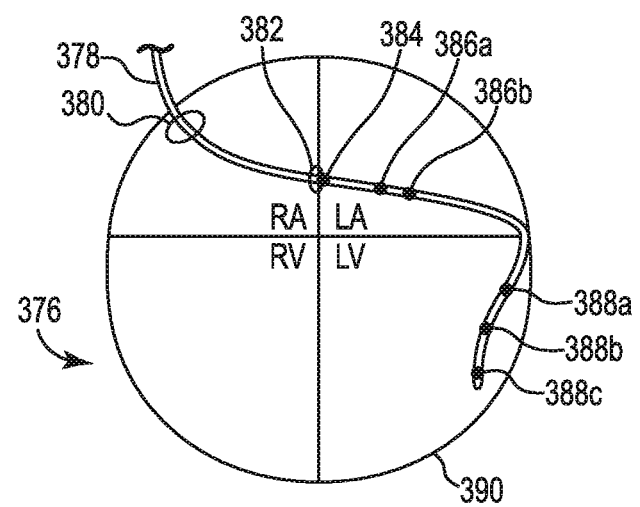
FIG. 3E is an illustration of another exemplary placement of a single pass implantable lead in a patient's heart in accordance with embodiments of the present disclosure.

FIG. 3E is an illustration 354 of an exemplary embodiment, illustrating placement of a single pass implantable lead 378 in a patient's heart 390 and utilized to treat certain types of cardiac conditions, such as left bundle branch block, CRT and the like. The illustration 376 shows the heart 390 broken into the four quadrants: right atrium (RA), right ventricle (RV), left atrium (LA), and left ventricle (LV). The single pass implantable lead 378 is shown entering the heart 390 via the superior vena cava 380, and routed epicardially around the left atrium (LA) through the coronary sinus ostium (CS OS) 382. A region of the single pass implantable lead 378 around the left atrium (LA) includes a plurality of proximal electrodes 384 and 386. In one embodiment, proximal electrode 384 may be anchored in and/or contact the coronary sinus (CS) at the coronary sinus ostium (CS OS) 382 and may operate to sense and/or pace the right atrium (RA). Additionally, in one embodiment, proximal electrodes 386 may be anchored in and/or contact the great cardiac vein (GCV) or coronary sinus (CS) in a way to be adjacent to the myocardium of the left atrium (LA) or may be anchored in and/or contact the myocardial sleeve of the CS and GCV, and may operate to sense and/or pace the left atrium (LA). From this position, the single pass implantable lead 378 is further routed through the vasculature of the heart 390 such that the one or more distal electrodes 388 are routed through the lateral or posterior coronary veins such that one or more of the distal electrodes 388 are positioned adjacent the left ventricle (LV). These one or more distal electrodes 388 operate to sense and/or pace the left ventricle (LV). The region of the single pass implantable lead 378 that is routed between the proximal electrodes (384 and 386) and the distal electrodes (388) is an intermediate portion (see discussion above).

Figure 3F:
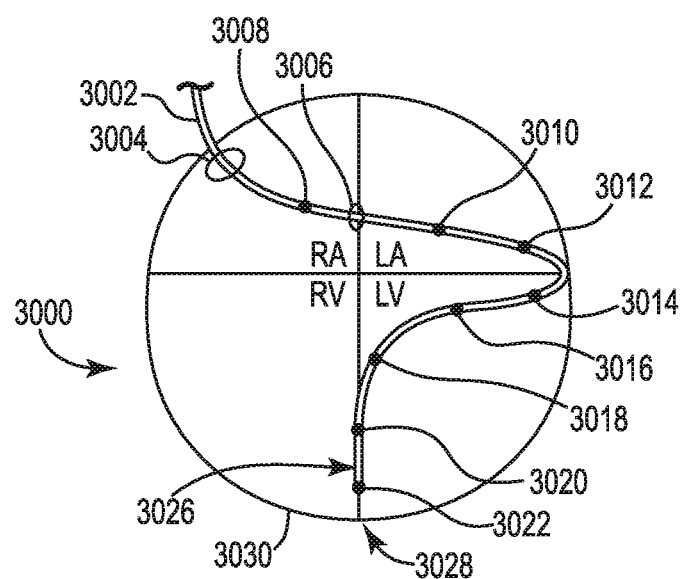
FIG. 3F is an illustration of another exemplary placement of a single pass implantable lead in a patient's heart in accordance with embodiments of the present disclosure.
Figure 3G:
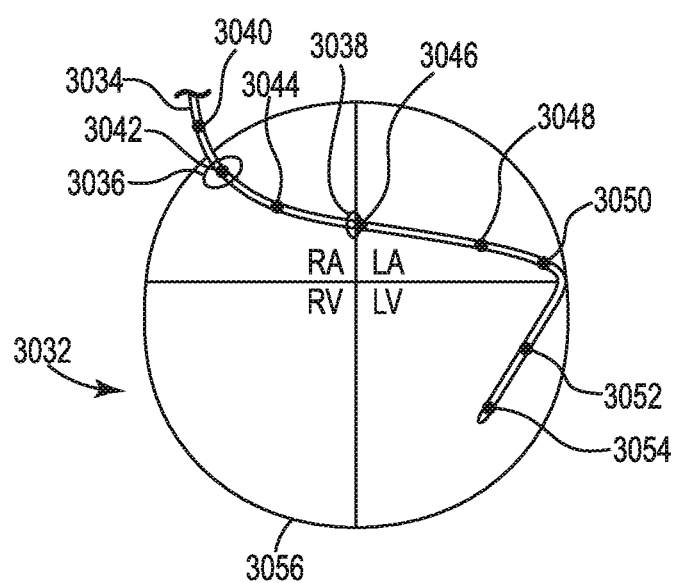
FIG. 3G is an illustration of another exemplary placement of a single pass implantable lead in a patient's heart in accordance with embodiments of the present disclosure.

Referring now FIGS. 3F and 3G, exemplary embodiments are provided, illustrating that the same single pass implantable lead (though indicated by different numerals 3002 and 3034, 3002 and 3034 for purposes of this example are in-fact representative of the same single pass implantable lead) may be implanted in a patient's heart at different locations in the anatomy. For example, in FIG. 3F, the single pass implantable lead 3002 is positioned within the patient's heart in a first position (the distal end of the lead is positioned within the anterior coronary branch), while the single pass implantable lead 3034 in FIG. 3G is positioned within the patent's heart in a second position (the distal end of the lead is positioned within either the posterior or lateral branch). Accordingly, in various embodiments, the various electrodes may be assigned to a respective chamber of the heart depending on their physical location after the single pass implantable lead has been implanted. For example, in FIG. 3F electrode 3012 is positioned within the coronary sinus adjacent the patient's left atrium, while in FIG. 3G electrode 3044 (which for purposes of this example is the same electrode as electrode 3012) is positioned within the patient's right atrium. Similarly, in FIG. 3F distal electrodes 3020 and 3022 are positioned within the anterior coronary branch, while in FIG. 3G distal electrodes 3052 and 3054 are positioned in a coronary branch different from the anterior coronary branch (e.g., the posterior or lateral branch). In these examples, it is evident that the same electrode may also be selected to perform different functions based on its physical location. For example, in FIG. 3G electrode 3044 may operate as a floating electrode that is selected to sense the function of the patient's right atrium, while electrode 3012 in FIG. 3F may operate to pace the patent's left atrium (or alternatively pace and sense the patient's left atrium) Thus, in various embodiments, the positioning of the single pass implantable lead and the corresponding location of the electrodes thereon may be determinative of what function is selected for those electrodes to perform.

In certain embodiments, the designation of an electrode's function may be determined after the single pass implantable lead is implanted. For example, after implanting the single pass implantable lead, the electrodes are tested (e.g., signals are delivered to the surrounding tissue) and any resulting signals (e.g., tissue stimulation) are recorded or observed. This procedure operates to identify the positioning of the respective electrodes within the anatomy. This procedure may be performed for each of the electrodes, or some subset of the electrodes (e.g., sequentially). In one embodiment, once the positioning of the electrodes within the anatomy is known, each of the electrodes (or some subset thereof) is tested for its efficiency, capacity, and/or performance in sensing and pacing the respective heart chamber (or surrounding tissue). In various embodiments, the system is programmed (e.g., VDD mode, DDD mode, etc) and tailored to accommodate the patient's needs.

Figure 4A:
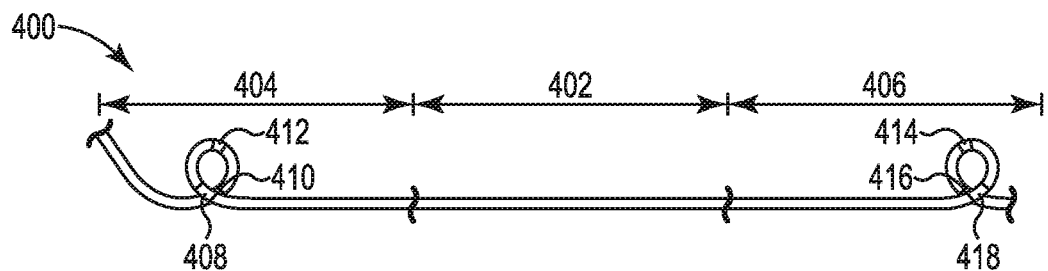
FIG. 4A is a schematic view of an exemplary single pass implantable lead having an adjustable intermediate region in accordance with embodiments of the present disclosure.

FIG. 4A is a schematic view of an exemplary single pass implantable lead 400 having an adjustable intermediate region 402 in accordance with embodiments of the present disclosure. The intermediate region 402 may comprise a flexible region that allows for damping of forces that may pull or push the single pass implantable lead 400 when implanted. As described in further detail below with reference to FIG. 5, a proximal region 404 and/or a distal region 406 of the single pass implantable lead 400 may include anchoring features that may be provided by biasing the proximal region 404 and the distal region 406. In addition, the proximal region 404 and the distal region 406 respectively include proximal electrodes 408, 410, 412 and distal electrodes 414, 416, 418. Although the single pass implantable lead 400 is shown as including three proximal electrodes 408, 410, 412 and three distal electrodes 414, 416, 418, other electrode quantities are also contemplated. The proximal region 404 and the distal region 406 may be biased, as shown in FIG. 4A, to contact a vessel wall and provide anchoring of the proximal region 404 and the distal region 406 thereto. Anchoring in this manner may be atraumatic to the vessel wall. As a result of the adjustable intermediate region 402 comprising a flexible material that allows for the adjustable intermediate region 402 to compress and stretch (and/or expand and contract), forces that may alter or displace the anchoring function of the proximal region 404 and the distal region 406 are dampened or absorbed by the adjustable intermediate region 402, which enhances anchoring and accurate placement of the single pass implantable lead 400. In addition, the adjustable intermediate region 402 may be adjustable by including a material composition having a lower durometer than the proximal region 404 and the distal region 406. Alternatively or in addition thereto, the adjustable intermediate region 402 may be adjustable by including a material composition having a lesser thickness than the proximal region 404 and the distal region 406. As a result, the adjustable intermediate region 402 may have a greater flexibility and/or elasticity than the proximal region 404 and the distal region 406.

Figure 4B:
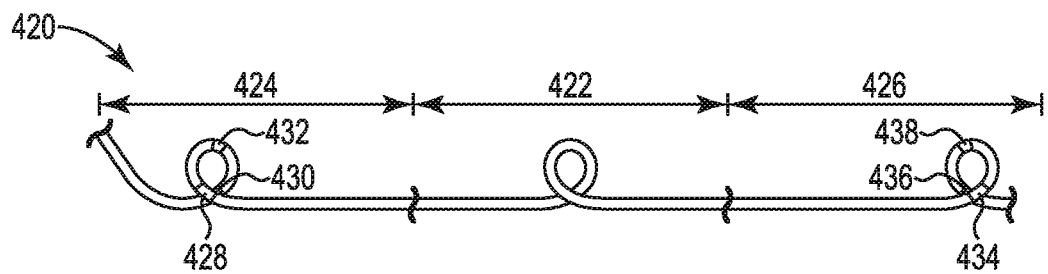
FIG. 4B is a schematic view of another exemplary single pass implantable lead having an adjustable intermediate region in accordance with embodiments of the present disclosure.

FIG. 4B is a schematic view of another exemplary single pass implantable lead 420 having an adjustable intermediate region 422 in accordance with embodiments of the present disclosure. As shown in FIG. 4B, the intermediate region 422 may comprise slack, similar to an accordion or coil, that allows for damping of forces that may pull or push the single pass implantable lead 420 when implanted. A proximal region 424 and a distal region 426 of the single pass implantable lead 420 may include biased portions having, respectively, proximal electrodes 428, 430, 432 and distal electrodes 434, 436, 438. The slack in the intermediate region 422 allows for the proximal electrodes 428, 430, 432 and the distal electrodes 434, 436, 438 to remain in contact with a vessel wall by way of the intermediate region 422 absorbing or mitigation forces that may displace the anchoring provided by the biased portions of the proximal region 424 and the distal region 426. The biased portions of the proximal region 424 and the distal region 426 may provide anchoring of the single pass implantable lead 420 without having to puncture, penetrate, or cause damage to the vessel wall of the heart, i.e., anchoring may be achieved in an atraumatic manner.

Figure 4C:
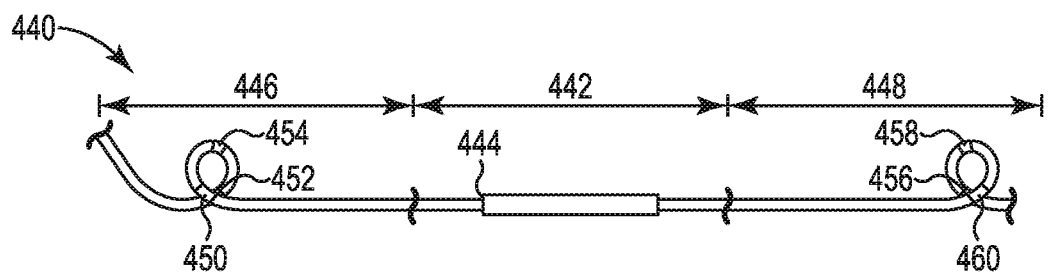
FIG. 4C is a schematic view of an exemplary single pass implantable lead having a telescoping intermediate region in accordance with embodiments of the present disclosure.

FIG. 4C is a schematic view of an exemplary single pass implantable lead 440 having a telescoping intermediate region 442 in accordance with embodiments of the present disclosure. As shown in FIG. 4C, the telescoping intermediate region 442 includes at least one overlapping region 444 of material that allow for the telescoping intermediate region 442 to stretch and contract. In this manner, the telescoping intermediate region 442 allows for damping of forces that push and pull on the single pass implantable lead 440. Portions on the single pass implantable lead 440 on either side of the telescoping intermediate region 442 may be configured to translate in and out of the telescoping intermediate region 442. In certain instances, only a distal region of the single pass implantable lead 440 may telescope in and out of the telescoping intermediate region 442. In other instances, only a proximal region of the single pass implantable lead 440 may telescope in and out of the telescoping intermediate region 442. As a result, the telescoping intermediate region 442 allows for stable placement of a proximal region 446 and a distal region 448 of the single pass implantable lead 440. The proximal region 446 and the distal region 448 may include biased portions having, respectively, proximal electrodes 450, 452, 454 and distal electrodes 456, 458, 460. The biased portions may ensure that the proximal electrodes 450, 452, 454 and the distal electrodes 456, 458, 460 contact, and are anchored to, a vessel wall of the heart in a way that at least one electrode contacts the myocardium wall side of the LA and LV. Anchoring in this manner may be atraumatic to the vessel wall. The telescoping intermediate region 442 a length adjustment of the single pass implantable lead 440, which enhances the ability of the anchoring provided by the biased portions of the proximal region 446 and the distal region 448. Although not explicitly shown, the thickness of the proximal region 446 and the distal region 448 may be equal. In other instances, the thickness of the proximal region 446 may be greater than the thickness of the distal region 448, and vice versa.

Figure 4D:
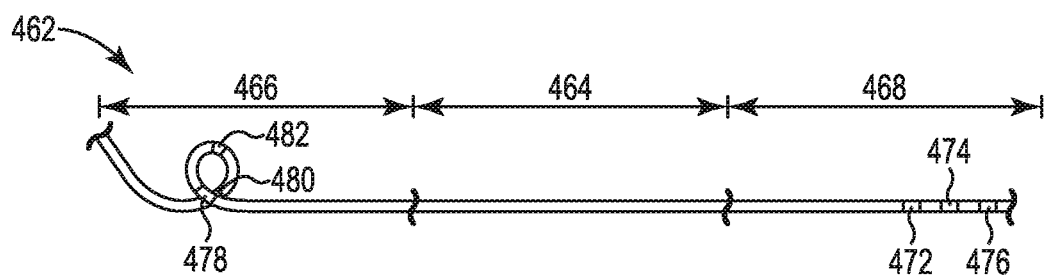
FIG. 4D is a schematic view of an exemplary single pass implantable lead and intermediate region in accordance with embodiments of the present disclosure.

FIG. 4D is a schematic view of an exemplary single pass implantable lead 462 and intermediate region 464 in accordance with embodiments of the present disclosure. As shown in FIG. 4D, the proximal region 466 and the distal region 468 include proximal electrodes 478, 480, 482 and distal electrodes 472, 474, 476. The distal region 468 may include a tine configured to anchor the distal region 468 to a vessel wall. The proximal region 466 is shown as having a biased portion which is configured to anchor the proximal region 466 to the vessel wall. Although not explicitly shown, the proximal region 466 may also include a tine configured to anchor the proximal region 466 to the vessel wall. Further, the proximal region 466 and/or the distal region 468 may include a bias to enhance contact of the proximal electrodes 478, 480, 482 and distal electrodes 472, 474, 476 against the vessel wall in a way that at least one electrode contacts the myocardial wall side of the vessel 510 in FIG. 5. Anchoring in this manner may be atraumatic to the vessel wall In each of the arrangements shown in FIGS. 4A-4D, the illustrative single pass implantable lead is not intended to suggest any limitation as to the scope of use or functionality of embodiments of the present invention. Neither should the illustrative single pass implantable lead be interpreted as having any dependency or requirement related to any single component or combination of components illustrated therein. Additionally, any one or more of the components depicted in FIG. 4 may be, in embodiments, integrated with various ones of the other components depicted therein (and/or components not illustrated), all of which are considered to be within the ambit of the present invention. For example, the single pass implantable lead 400, shown in FIG. 4A, may include a tine, or a telescoping intermediate region as is shown in FIG. 4C.

Figure 5:
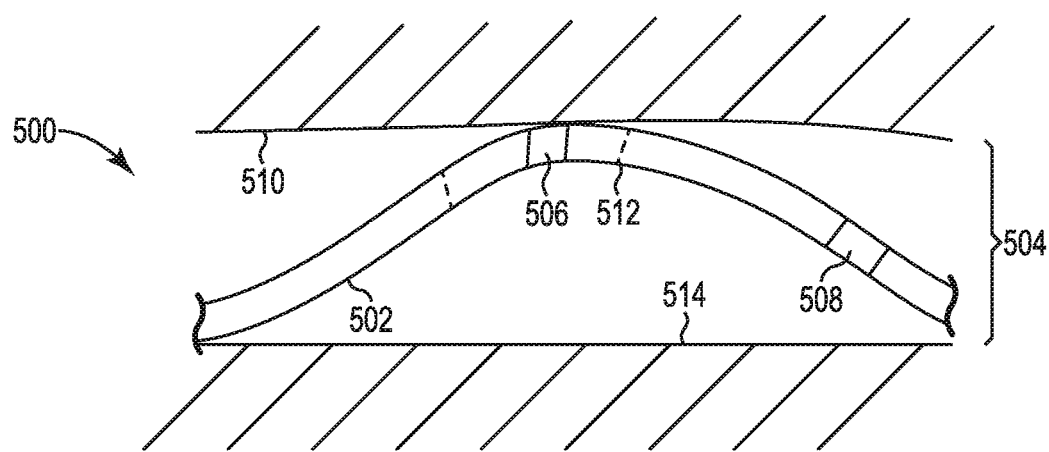
FIG. 5 is an enlarged schematic view of a region of an exemplary single pass implantable lead in accordance with embodiments of the present disclosure.

FIG. 5 is an enlarged schematic view of a region 500 of an exemplary single pass implantable lead 502 in accordance with embodiments of the present disclosure. As shown in FIG. 5, the implantable lead 502 is inserted at a target region within a blood vessel 504. The enlarged region 500 of the implantable lead 502 shown may be either a proximal region or a distal region of the implantable lead 502 as discussed above with reference to FIGS. 2, and 4A-D.

Each region 500 of the implantable lead 502 may include one or more electrodes. As shown in FIG. 5, the region 500 includes two electrodes 506, 508, each of which may be coupled to a corresponding cable conductor or coil conductor within the interior of the lead 502. An implantable medical device such as a pulse generator may supply electrical pulses to the electrodes 506, 508 for pacing one or more regions (or chambers) of the heart and/or for sensing cardiac electrical activity. Similarly, the implantable medical device may supply electrical pulses to electrodes in the other region of the implantable lead 502 (not shown) for pacing one or more other regions (or chambers) of the heart and/or for sensing cardiac electrical activity.

In one embodiment, each region 500 of the implantable lead 502 may be configured to anchor within the vessel 504. Each region 500 of the implantable lead 502 may be configured to anchor by pre-biasing of one or more portions of the implantable lead 502. Pre-biasing of one or more portions (either one of or both of the proximal region and the distal region) may configure the implantable lead 502 to engage a wall of blood vessel to secure the implantable lead 502 in a location along the vessel. Engagement of the blood vessel wall may be such that the vessel wall is not penetrated by the lead 502. The biasing may occur by way of a material transition region 512 that provides a natural turn or curve in the implantable lead 502 due to the transition. The material transition region 512 may be provided proximal or distal to at least one of the electrodes 506, 508. The material transition region may be the result of the implantable lead 502 transitioning between polyurethane and silicone. The anchoring allows for positioning of the implantable lead 502 within the vessel 504. As shown in FIG. 5, the implantable lead 502 is anchored against the myocardial wall side 510 of the vessel rather than the myocardium-free wall side 514 of the vessel 504. As a result, the implantable lead 502 may be secured in place such that the electrodes 506, 508 contact the myocardial wall side 510 of the vessel 504 to provide pacing to the desired cardiac chamber (e.g., LA or LV) and/or for sensing cardiac electrical activity.

As discussed above, and as illustrated herein, in various embodiments, the implantable lead includes a plurality of proximal electrodes and plurality of distal electrodes. In one embodiment, one or more electrodes of the plurality of proximal electrodes may be designed to operate as pacing electrodes, while one or more other electrodes of the plurality of proximal electrodes may be designated to operate as sensing electrodes.

In one embodiment, the system is configured to select the electrodes (or combination of electrodes) that are designated to operate as pacing electrodes based on some predetermined criteria, such as a pacing threshold (e.g., an amount of energy required to successfully pace a target region of the heart). In one such embodiment, as discussed in greater detail below, the pacing threshold associated with a particular plurality of electrodes may be analyzed individually and in combination to determine an optimal pacing configuration. In one embodiment, an electrode may be selected based on its associated pacing threshold being below a designated threshold value. In another embodiment, a combination of electrodes is configured to operate together based on their combined pacing threshold being below a designated threshold. In various embodiments, a designation of pacing and sensing electrodes is completed for each target region of the heart.

Figure 6:
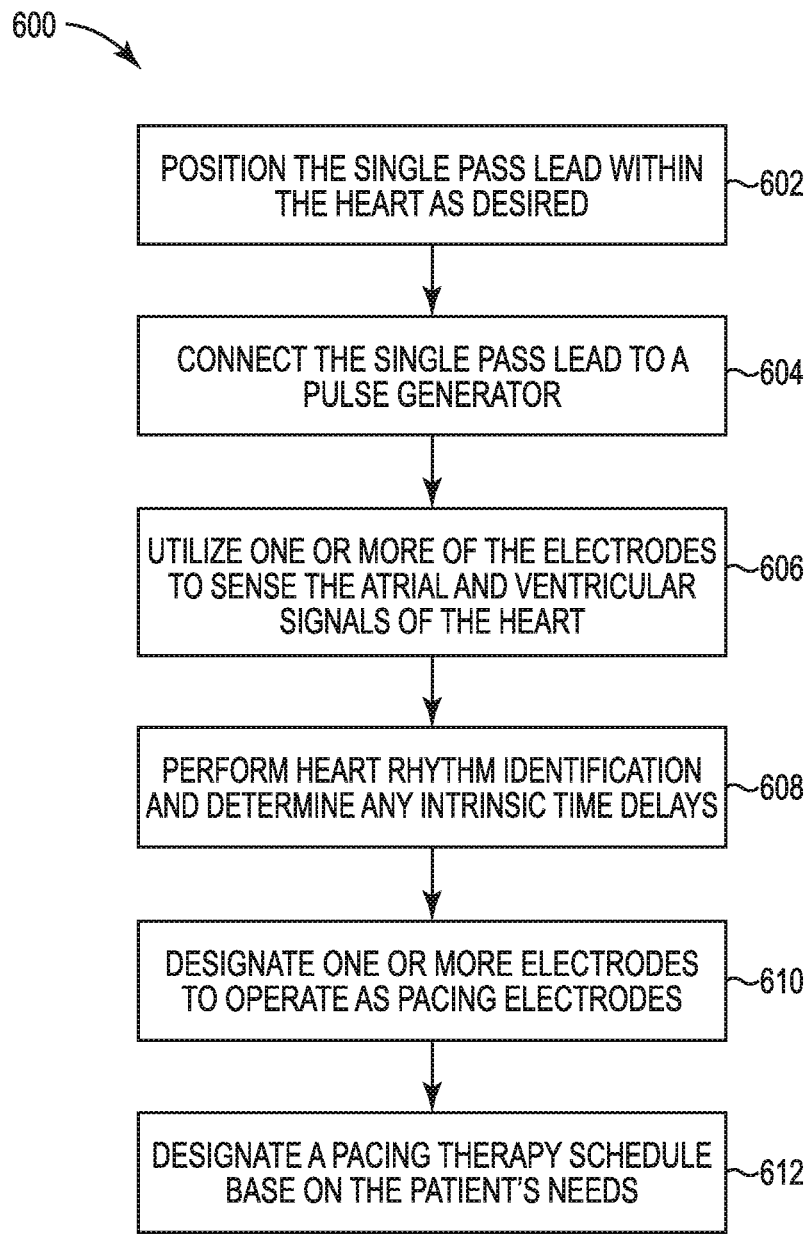
FIG. 6 is an exemplary flowchart illustrating a method of implanting a single pass implantable lead in accordance with embodiments of the present disclosure.

For example, referring now to the exemplary flowchart 600 of FIG. 6 illustrating a method of implanting and configuring a single pass implantable lead, in one embodiment, the single pass lead is positioned within the heart as desired at block 602. In one embodiment, the single pass lead is positioned within the heart based on the patient's heart condition (e.g., bradyarrhythmia, tachyarrhythmia, heart failure). In one embodiment, block 602 includes positioning a floating electrode within the right atrium (RA) and/or positioning another electrode at the coronary sinus ostium (CS OS) in the coronary sinus (CS) to sense and pace the right atrium (RA). In one embodiment, block 602 also includes positioning one or more electrodes within the coronary sinus (CS) or the great cardiac vein (GCV) adjacent the myocardium of the left atrium (LA) or may be anchored in and/or contact the myocardial sleeve of the CS and GCV to sense and pace the left atrium (LA). In one embodiment, block 602 also includes positioning one or more distal electrodes within the anterior coronary branch adjacent to the septum separating the right and left ventricles to sense and pace both the right ventricle (RV) and the left ventricle (LV) (e.g., in a bradyarrhythmia case).

Once properly positioned within the heart, the single pass lead is connected to a pulse generator at block 604. The pulse generator operates in accordance with the single pass lead to both sense and pace the patient's heart. At block 606 one or more of the plurality of electrodes are initially utilized (either individually or in some combination) to sense the atrial signal of the heart, and one or more of the plurality of electrodes are initially utilized (either individually or in some combination) to sense the ventricular signal of the heart. For example, referring back to FIG. 3D, in one embodiment, electrode 362 is initially utilized to sense the right atrium (RA), electrode 366a is initially utilized to sense the left atrium (LA), and electrode 368a is initially utilized to sense both the right and left ventricles. It should be appreciated, however, that more than one electrode may be initially utilized to sense a particular region of the heart. For example, in one embodiment, electrodes 366a and 366c may be initially utilized to sense the left atrium (LA).

Referring back now to FIG. 6, at block 608 the system performs heart rhythm identification and determines any associated timing delays (e.g., to account for an intrinsic right atrium (RA) to left atrium (LA) delay, or atrial to ventricular delay). At block 610, the system designates which electrodes are to operate as pacing electrodes. In one embodiment, the system cycles through and analyzes each electrode in the order in which it is positioned along the single pass lead. In another embodiment, the system analyzes a grouping of electrodes that are designated for sensing and/or pacing a particular region of the heart (such as the left atrium (LA)). In yet other embodiments, the electrodes are analyzed based on one or more determinations made during the sensing phase of block 606. Thus, while the example discussed below illustrates a particular order, it should be appreciated that such disclosure shall not be interpreted as limiting and that the plurality of electrodes may be analyzed in any order without departing from the scope of the present disclosure.

In one embodiment, the electrodes are analyzed according to a predesignated association with a particular region of the heart. For example, referring to FIG. 3D, electrodes 362 and 364 are predesignated to sense and/or pace the right atrium (RA). Similarly, for example, electrodes 366a-366d are predesignated to sense and/or pace the left atrium (LA). Likewise, for example, electrodes 368a and 368b are predesignated to sense and/or pace both the right ventricle (RV) and the left ventricle (LV). In one embodiment, a determination is made as to which of electrodes 362 and 364 have the lowest pacing threshold for pacing the right atrium (RA). In one embodiment, because electrode 364 is situated at the coronary sinus ostium (CS OS) within the coronary sinus (CS) and electrode 362 is floating within the right atrium (RA), it is likely that electrode 364 will have a lower pacing threshold with regard to pacing the right atrium (RA) relative to electrode 362. Accordingly, if electrode 364 has such a lower pacing threshold, the system will designate electrode 364 as a pacing electrode. In one embodiment, the system may also designate electrode 364 as a sensing electrode (alone, or in combination with electrode 362).

In one embodiment, a determination is also made as to which of electrodes 366a-366d (either individually, or in combination) have the lowest (or alternatively, a desired) pacing threshold for pacing the left atrium (LA). In one embodiment, such a determination is made by attempting to pace the left atrium (LA) with each of electrodes 366a-366d individually. In one embodiment, the system additionally analyzes combinations of the electrodes 366a-366d to determine if a particular combination of electrodes 366a-366d has a desirably low pacing threshold. In one embodiment, a single one of electrodes 366a-366d (such as electrode 366a) may be associated with a desired pacing threshold. In another embodiment, a combination of less than all of electrodes 366a-366d (such as electrode 366b and 366c combined as the anode) may be associated with a desired pacing threshold. In yet another embodiment, a combination of all of the electrodes 366a-366d may be associated with a desired pacing threshold. Specifically, a combination of two or more electrodes selected as anodes may decrease the pacing threshold of another one of the electrodes selected as the cathode. For example, electrode 366a and electrode 366b are selected and combined as the anode and electrode 366c is selected as the cathode, wherein the configuration will decrease the pacing threshold of electrode 366c. In another example, two or more electrodes (such as electrodes 366a and 366b) are selected as the cathode in order to increase the chance of myocardium contact. In such an example, the anode will be the PG or some other electrode(s) along the single pass implantable lead.

In such embodiments, the system determines which configuration of one or more of the electrodes is associated with the most desirable pacing threshold. It should be appreciated that the configuration selected may not be that configuration having the lowest pacing threshold, but may instead be a configuration that has a pacing threshold below a designated pacing threshold that utilizes a desired quantity and/or location of the electrodes 366a-366d. Thus, in some embodiments, both the pacing threshold and the required quantity of electrodes associated with that pacing threshold are considered when making such a determination. In certain embodiment, two or more pacing sites may be utilized in the RA and/or the LA to suppress and/or prevent, for example, atrial tachycardia.

In one embodiment, a determination is also made as to which of electrodes 368a and/or 368b (either individually, or in combination) have the lowest (or alternatively, a desired) pacing threshold for pacing the right ventricle (RV) and the left ventricle (LV) (e.g., in a bradyarrhythmia case). In one embodiment, such a determination is made by attempting to pace the right and left ventricles with each of electrodes 368a and 368b individually. In one embodiment, the system additionally tests electrodes 368a and 368b in combination to determine if the combination of electrodes has a desirably low pacing threshold. In such embodiments, the system determines which configuration of one or more of the electrodes is associated with the most desirable pacing threshold. As discussed above, it should be appreciated that the configuration selected may not be that configuration having the lowest pacing threshold, but may instead be a configuration that has a pacing threshold below a designated pacing threshold that utilizes a desired quantity and/or location of the electrodes. For example, referring back to FIG. 3E, electrodes 388a, 388b, and 388c may be selected based on a patient's hemodynamic response to various pacing configuration tests. It should be appreciated that the configuration of electrodes selected for various pacing schemes may be subsequently altered (and a different configuration of selected electrodes may be selected for pacing) based on remodeling changes after long-term CRT therapy.

Referring back now to FIG. 6, at block 612 the system designates a pacing therapy schedule based on the patient's needs. In one embodiment, the system selects one of a plurality of prearranged pacing therapy schedules. In another embodiment, the system determines a pacing therapy schedule unique to the patient based on the intrinsic hemodynamics of the patient's heart (e.g., accounting for intrinsic time delays and the like). In yet another embodiment, the system modifies a prearranged pacing therapy schedule to conform to the needs of the patient. In one example embodiment, where a patient exhibits an abnormally long RA-LA delay, the system can be configured such that the electrodes on the single pass implantable lead are designated to emit a signal to pace the LA after an RA contraction has been sensed. Such a procedure may operate to shorten the RA-LA delay and improve overall hemodynamics.

As discussed above, the single pass lead includes a plurality of electrodes. In one embodiment, each of the electrodes of the single pass lead is uni-polar electrodes that operate with one or more other electrodes, or the pulse generator itself to deliver pacing signals. In another embodiment, each of the electrodes of the single pass lead is a bi-polar electrode. In yet another embodiment, one or more of the electrodes of the single pass lead is a uni-polar electrode and one or more other electrodes of the single pass lead is a bi-polar electrode.

Additionally, as discussed above, two or more of the electrodes may be utilized in combination to deliver a pacing signal. In one such embodiment, one of the electrodes operates as the anode, while another one of the electrodes operates as the cathode. In another such embodiment, a plurality of the electrodes operate as the anode, while another one of the electrodes operates as the cathode. In yet another such embodiment, one of the electrodes operates as the anode, which a plurality of the other electrodes operate as the cathode. In yet another such embodiment, a plurality of the electrodes operate as the anode, while a plurality of the other electrodes operate as the cathode. It should thus be appreciated that any number and associated combination of electrodes may be utilized to deliver pacing signals to the desired regions of the heart without departing from the scope of the present disclosure.

Additionally, as discussed above, in various embodiments, one or more of the electrodes may operate to both sense and pace a targeted region of the patient's heart. For example, referring back to FIG. 3C, in one embodiment, electrode 340 (which is positioned at the coronary sinus ostium (CS OS) within the coronary sinus (CS)) operates to both sense the right atrium (RA) and pace the right atrium (RA). Likewise, electrode 342 (which is positioned within the coronary sinus (CS) adjacent the myocardium of the left atrium (LA) or may be anchored in and/or contact the myocardial sleeve of the CS and GCV) operates to both sense the left atrium (LA) and pace the left atrium (LA). Moreover, regardless of whether there are a plurality of electrodes available for sensing and pacing a particular region of a patient's heart, in some embodiments, a subset of those electrodes may be utilized to do so. For example, despite single pass lead 334 including a plurality of distal electrodes 344a and 344b, the system may only operate to utilize distal electrode 344a to sense and pace both the left and right ventricles.

In one embodiment, such a configuration may arise as a result of a malfunctioning electrode (i.e., electrode 344b does not sufficiently sense and/or pace the left and right ventricles). In another embodiment, such a configuration may arise as a result of the patient's heart condition changing in some manner that renders one of the electrodes ineffective (such as through a deterioration of the tissue surrounding the electrode, or through increased resistance or the like). Importantly, under these types of conditions, the system is operable to determine that one or more of the sensors is ineffective (or have become ineffective) and, as a result, modify the pacing and/or sensing configuration of the electrodes (by designating another one of the electrodes to assume a pacing and/or sensing role). Such versatility provides for a reliable and long-lasting system that can accommodate unpredictable dynamic changes in a patient's heart including myocardial ischemic events, cardiac remodeling, etc. without a need to manipulate the positioning of the lead or the electrodes on the lead.

It should also be appreciated that the above-discussed structure and orientation of electrodes on the proximal and distal regions of the single pass lead may be utilized in any of the embodiments (or examples) disclosed herein. Further, the illustrations and corresponding descriptions thereof shall not be limiting in any respect. For example, the quantity of electrodes may be any desired quantity and may be situated along the single pass lead in any desired configuration, orientation, groupings and the like.

It should also be appreciated that arranging the single pass implantable lead in the heart as described avoids crossing the tricuspid and mitral valves of the patient. For example, the arranging the proximal region may include arranging a portion of the lead and one or more of the proximal electrodes in the patient's great cardiac vein (GCV) and coronary sinus (CS). From this position, the distal region and distal electrodes are further arranged in the patient's coronary branch.

As described, the certain embodiments of the system provide for a method of sensing and/or pacing a cardiac rhythm of the left and/or right atrium of the patient via one or more proximal electrodes. In other words, while possible, the system does not require both RA and the LA electrodes, and embodiments are envisioned wherein the system includes electrodes either the LA or the RA (but not both).

The positioning of the distal electrodes over the septum between the right and left ventricles (the intraventricular septum), as described above, provides for a method of sensing a cardiac rhythm of the left and right ventricles of the patient via one or more distal electrodes, and also provides for a method of pacing both the left and right ventricles of (biventricular pacing). In certain instances, transmitting a pacing signal via one or more of the distal electrode includes transmitting a pacing signal into the septum between the right and left ventricles (the intraventricular septum), wherein the signal propagates down the intraventricular septum to the mid-to-apex of the heart, causing stimulation of the surrounding tissue and thereby causing the left and right ventricles to contract. Or a pacing signal transmits through both right and left ventricular myocardium, wherein the signal propagates to both ventricles to cause contract simultaneously. In other words, both the right ventricle (RV) and the left ventricle (LV) are intentionally paced.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of pacing a patient's heart using an implantable lead including a plurality of proximal electrodes and a plurality of distal electrodes, the implantable lead having a proximal region including at least one of the plurality of proximal electrodes positioned in a coronary sinus or great cardiac vein of the patient's heart and a distal region positioned in a coronary vein of the patient's heart such that at least one of the plurality of distal electrodes is situated proximate an intraventricular septum of the patient's heart, the method comprising:
   sensing an atrial and a ventricular signal of the patient's heart via at least one of the proximal electrodes and at least one of the distal electrodes, respectively;
   determining a pacing threshold associated with each of the plurality of distal electrodes;
   selecting at least one of the plurality of distal electrodes that have associated therewith right and left ventricular pacing thresholds; and
   delivering a pacing signal to the patient's heart via the selected at least one distal electrode, the transmitted pacing signal causing a desired contraction of both the right ventricle and the left ventricle.

2. The method of claim 1, wherein the distal region of the implantable lead is positioned within an anterior coronary vein.

3. The method of claim 1, wherein selecting the at least one of the plurality of distal electrodes includes selecting at least one distal electrode having associated therewith right and left ventricular pacing thresholds below a designated maximum pacing threshold value.

4. The method of claim 1, wherein determining the pacing threshold associated with each of the plurality of distal electrodes further comprises determining a right and left ventricle pacing threshold associated with a first one of the plurality of distal electrodes and determining a right and left ventricle pacing threshold associated with a second one of the plurality of distal electrodes.

5. The method of claim 4, wherein the first one of said plurality of distal electrodes has associated therewith first right and left ventricular pacing thresholds and the second one of the plurality of distal electrodes has associated therewith second right and left ventricular pacing thresholds, the second right and left ventricular pacing thresholds exceeding said first right and left ventricular pacing thresholds.

6. The method of claim 1, further comprising selecting a first one of the plurality of distal electrodes as a right and left ventricular pacing electrode.

7. The method of claim 6, further comprising selecting the first one of the plurality of distal electrodes or a second one of the plurality of distal electrodes as a right and left ventricular sensing electrode.

8. The method of claim 1, further comprising selecting a first one of the plurality of distal electrodes and a second one of the plurality of distal electrodes to operate, in combination, to pace a right ventricle and a left ventricle of the patient's heart.

9. The method claim 8, wherein selecting the first one of the plurality of distal electrodes and the second one of the plurality of distal electrodes to operate, in combination, to pace a right ventricle and a left ventricle of the patient's heart is based on left and right ventricular pacing thresholds associated with the first and said second ones of the plurality of distal electrodes, in combination, being less than the right and left ventricular pacing thresholds of the first and the second one of the plurality of distal electrodes, individually.

10. The method of claim 1, wherein a first group of the plurality of proximal electrodes is disposed along the implantable lead distal to the at least one proximal electrodes positioned in the coronary sinus or the great cardiac vein of the patient's heart, and wherein the method further comprises determining a left atrial pacing threshold associated with a first one of the first group of the plurality of proximal electrodes, and determining a left atrial pacing threshold associated with a second one of said the first group of the plurality of proximal electrodes, wherein the second determined left atrial pacing threshold exceeds the first determined left atrial pacing threshold, and selecting the first one of the first group of the plurality of proximal electrodes as a left atrial pacing electrode based on the second determined left atrial pacing threshold exceeding the first determined left atrial pacing threshold.

11. The method of claim 10, further comprising selecting the first one of the first group of the plurality of proximal electrodes or the second one of the first group of the plurality of proximal electrodes as a left atrial sensing electrode.

12. The method of claim 10, further comprising selecting the first one of the first group of the plurality of proximal electrodes and the second one of the first group of the plurality of proximal electrodes to operate, in combination, to pace the left atrium of the patient's heart.

13. A method of inserting an implantable lead into a patient's heart, the implantable lead having a proximal region including a plurality of proximal electrodes and a distal region including at least one distal electrode, the method comprising:
  inserting the implantable lead into the patient's heart via a superior vena cava or an inferior vena cava;
  positioning the implantable lead such that at least a portion of the proximal region of the single pass implantable lead is positioned within a coronary sinus of the patient's heart and at least a portion of the distal region of the single pass implantable lead is positioned within an anterior coronary vein, with the at least one distal electrode being positioned adjacent to an intraventricular septum of the patient's heart;
  electrically connecting the single pass implantable lead to a pulse generator or an implantable medical device;
  selecting a first proximal electrode from the plurality of proximal electrodes to operate as a right atrial pacing electrode based on a measured right atrial pacing threshold associated with the first proximal electrode;
  selecting a second proximal electrode from the plurality of proximal electrodes to operate as a left atrial pacing electrode based on a measured left atrial pacing threshold associated with the second proximal electrode; and
  selecting a first distal electrode from the at least one distal electrode to operate as a right ventricular and left ventricular pacing electrode based on measured right and left ventricular pacing thresholds associated with the first distal electrode.

14. The method of claim 12, wherein the first proximal electrode is positioned proximate a coronary sinus ostium within the coronary sinus, and the second proximal electrode is positioned within the coronary sinus or a great cardiac vein and adjacent a myocardium of a left atrium.

15. The method of claim 13, wherein the plurality of proximal electrodes includes at least a third proximal electrode positioned proximate the second proximal electrode and wherein the second proximal electrode is selected based on the measured left atrial pacing threshold associated with the second proximal electrode being less than a measured left atrial pacing threshold associated with the third proximal electrode.

16. The method of claim 15, wherein the third proximal electrode is designated as a left atrial sensing electrode.

17. The method of claim 15, wherein the third proximal electrode is also selected as a left atrial pacing electrode such that the second and the third proximal electrodes operate together to deliver a pacing signal to the patient's heart, wherein a measured left atrial pacing threshold of the second and third proximal electrodes, in combination, being less than the measure left atrial pacing threshold of the second and third proximal electrodes individually.

18. The method of claim 13, wherein the plurality of proximal electrodes includes at least a fourth proximal electrode positioned along the single pass lead proximal of the first proximal electrode, the fourth proximal electrode being positioned within a right atrium and being designated as a right atrial sensing electrode.

19. A method of performing biventricular pacing of a patient's heart using an implantable lead including one or more proximal electrodes and one or more distal electrodes, the method comprising:
  positioning a proximal region of the implantable lead such that the one or more proximal electrodes are positioned in a coronary sinus or the great cardiac vein of the patient's heart;
  positioning a distal region of the implantable lead in an anterior coronary vein of the patient's heart such that the one or more distal electrodes are situated adjacent to an intraventricular septum of the patient's heart;
  sensing an atrial and a ventricular signal of the patient's heart via the one or more proximal electrodes and the one or more distal electrodes;
  selecting at least one distal electrode of the one or more distal electrodes having associated therewith right and left ventricular pacing thresholds below a designated pacing threshold;
  delivering, via a pulse generator coupled to the implantable lead, a pacing signal to the patient's heart via the selected at least one distal electrode, the delivered pacing signal causing a desired contraction of both the right ventricle and the left ventricle.

20. The method of claim 19, wherein the implantable lead includes a plurality of proximal electrodes, a first one of the plurality of proximal electrodes being positioned proximate the coronary sinus ostium of the patient's heart, the first one of the proximal electrodes being operable to sense and pace at least the right atrium of the patient's heart.

* * * * *